US006775007B2

(12) United States Patent
Izatt et al.

(10) Patent No.: US 6,775,007 B2
(45) Date of Patent: Aug. 10, 2004

(54) FREQUENCY-ENCODED PARALLEL OCT AND ASSOCIATED SYSTEMS AND METHODS

(76) Inventors: Joseph A. Izatt, 10505 Leslie Dr., Raleigh, NC (US) 27615; Andrew M. Rollins, 534 Miner Rd., Highland Heights, OH (US) 44143

( * ) Notice: Subject to any disclaimer, the term of this patent is extended or adjusted under 35 U.S.C. 154(b) by 163 days.

(21) Appl. No.: 10/059,723

(22) Filed: Jan. 29, 2002

(65) Prior Publication Data

US 2003/0025913 A1 Feb. 6, 2003

Related U.S. Application Data

(60) Provisional application No. 60/264,951, filed on Jan. 29, 2001.

(51) Int. Cl.[7] .................................................. G01B 9/02
(52) U.S. Cl. ...................................... 356/497; 356/479
(58) Field of Search ................................ 356/450, 497, 356/479; 351/205; 606/4, 10

(56) References Cited

U.S. PATENT DOCUMENTS 5,892,583 A * 4/1999 Li ............................... 356/450
6,198,540 B1 * 3/2001 Ueda et al. .................. 356/479
6,268,921 B1 * 7/2001 Seitz et al. .................. 356/407

FOREIGN PATENT DOCUMENTS

WO          WO0069333 A    11/2000

OTHER PUBLICATIONS

Rollins et al, "In vivo video rate optical coherence tomography", Jul. 23, 1998, Optic Express, pp. 219–229.
Rollins et al, "Optimal Interferometer designs for optical coherence tomography", Nov. 1, 1999, Optics Letters, vol. 24, No. 21, pp. 1484–1486.

Prodoleanu A.G. et al: "Simultaneous En–face Imaging of Two Layers in the Human Retina by Low–Coherence Reflectometry", Optics Letters, Optical Society of America, Washington, US, vol. 22, No. 13, Jul. 1, 1997, pp. 1039–1041, XP00065809.

Podoleanu A.G. et al: "Simultaneous Low Coherence Interferometry Imaging at Two Depths Using an Integrated Optic Modulator", Amsterdam, NL, vol. 191, No. 1–2, May 1, 2001, pp. 21–30, XP004234990.

Everett M.J. et al:"Non–invasive Diagnosis Of Early Carles With Polarization Sensitive Optical Coherence Tomography", Proceedings of the Spie, Spie, Bellingham, VA, us, vol. 3593, Jan. 24, 1999, pp. 177–182, XP000931184, Chapter 3, pp. 178–179, Figure 1.

Boer De J.F. et al: "Polarization Effects In Optical Coherence Tomography of Various Biological Tissues", IEEE Journal of Selected Topics In Quantum Electronics, IEEE Service Center, US., vol. 5, No. 4, Jul. 1999, pp. 1200–1203, XP00893469, Chapter III, pp. 1200–1201, Figure 1.

* cited by examiner

Primary Examiner—Frank G. Font
Assistant Examiner—Andrew H. Lee
(74) Attorney, Agent, or Firm—Renner, Otto, Boisselle & Sklar, LLP

(57) ABSTRACT

Rapid scan optical delay techniques are used in parallel implementation of OCT using a detector and signal processing can be carried out using algorithms. Frequency encoded parallel OCT and multi-path, frequency encoded reference delay networks are used. A large number of frequency-correlated depth channels are used to acquire multiple depth scans of a sample. A different frequency shift (Doppler shift) on each different path length, or delay, is used to obtain simultaneous respective signals and, thus, information about the sample, from different depths in the sample. Reference delay line functions are obtained using bulk optics, integrated optics and fiber optics.

27 Claims, 22 Drawing Sheets

3) BEST EMBODIMENT: RETROFLECTION (INCLUDING CIRCULATOR-BASED IMPROVEMENTS)

• IF MIRRORS ARE PLACED ACCURATELY, DELAY CHIP SHOULD BE RECIPROCAL => ALL LIGHT GOES BACK INTO REFERRENCE FIBER WITH DOUBLED DELAYS!

• IF MIRRORS ARE PLACED ACCURATELY, DELAY CHIP SHOULD BE RECIPROCAL => ALL LIGHT GOES BACK INTO REFERRENCE FIBER WITH DOUBLED DELAYS!

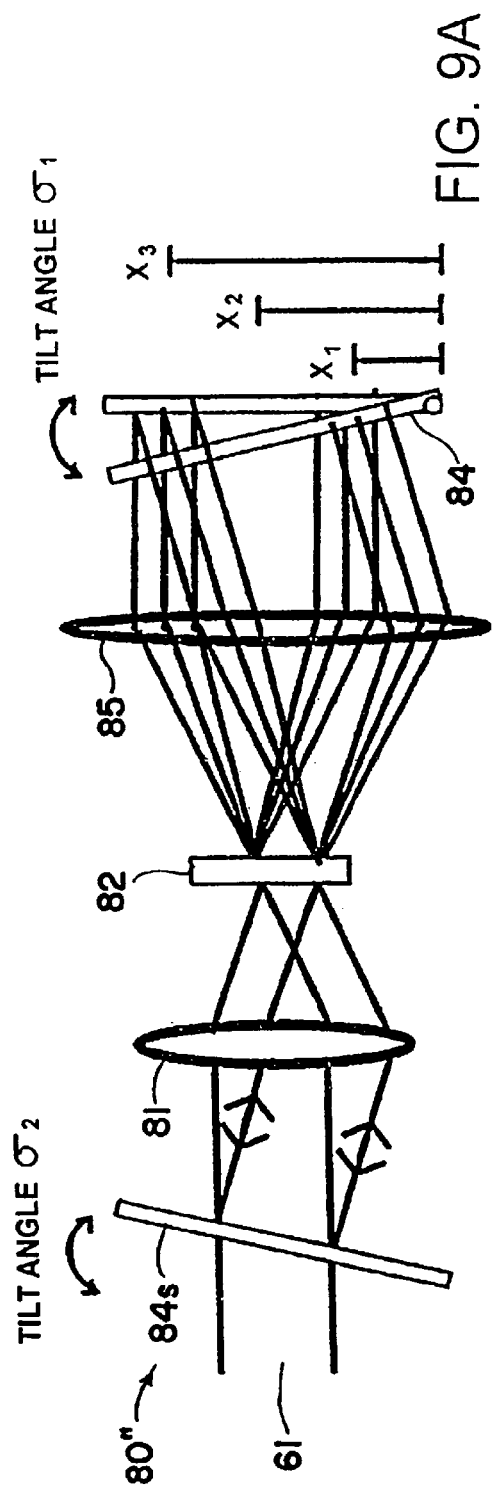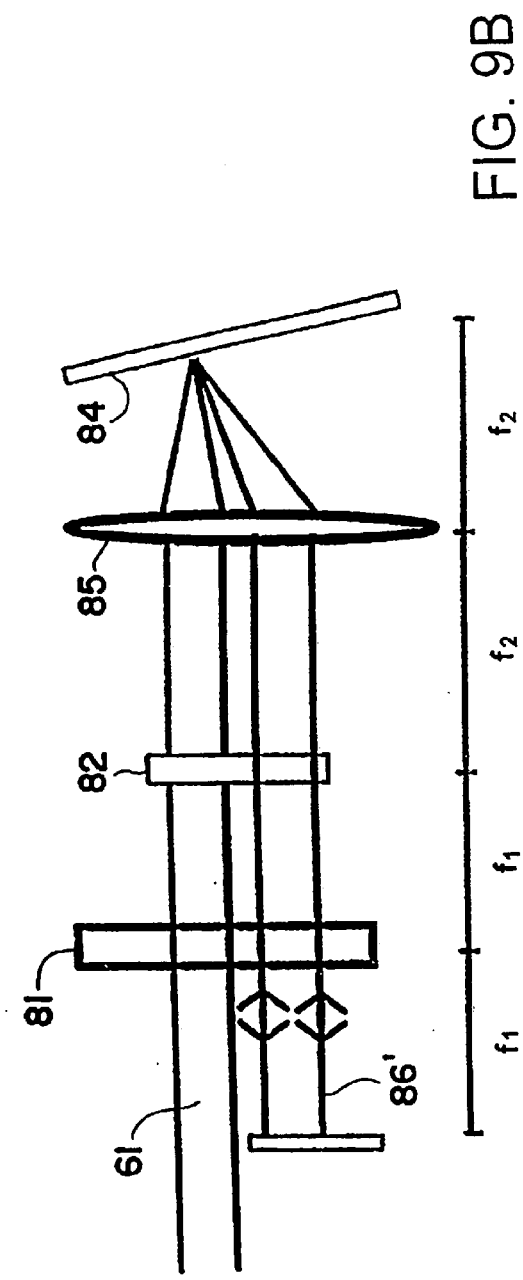
FIG. 9A
FIG. 9B

2) Electro-optic (fiber or integrated-optic implementation) or PZT (fiber stretching) using $2\pi$ linear sawtooth phase modulation:

$E_0(t) = \cos(\omega_c t + \theta_1 + \theta_2 + \theta_3 + \theta_4 + ...)$
$= \cos[(\omega_c + k_1 + k_2 + k_3 + k_4 + ...)t]$
= single-sideband frequency shift!

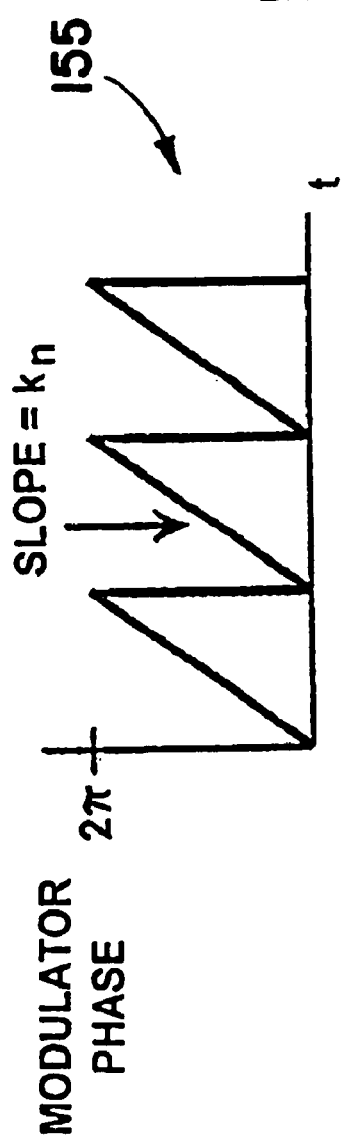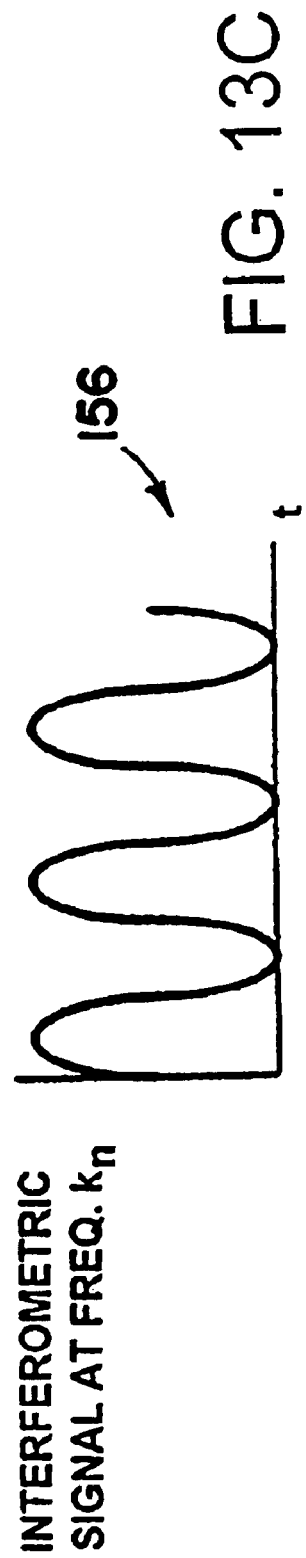

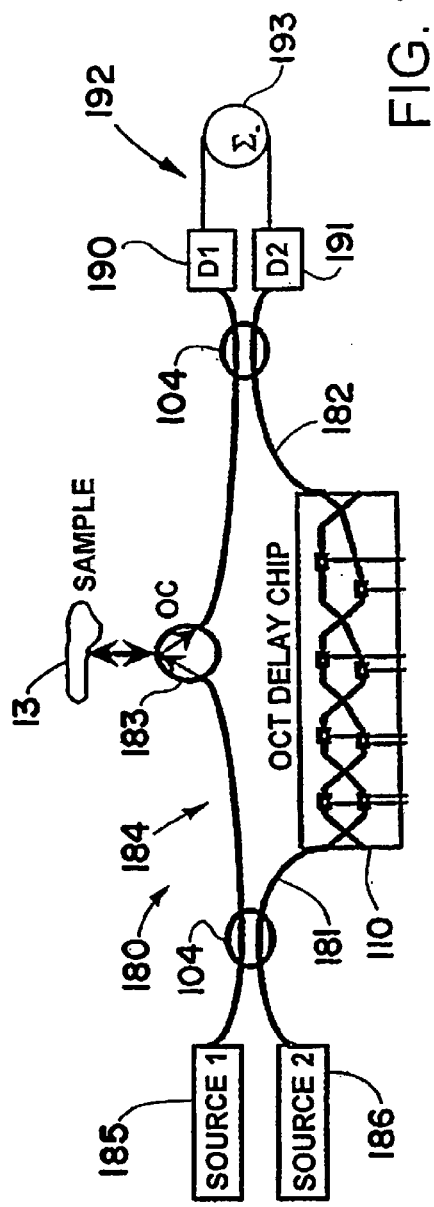
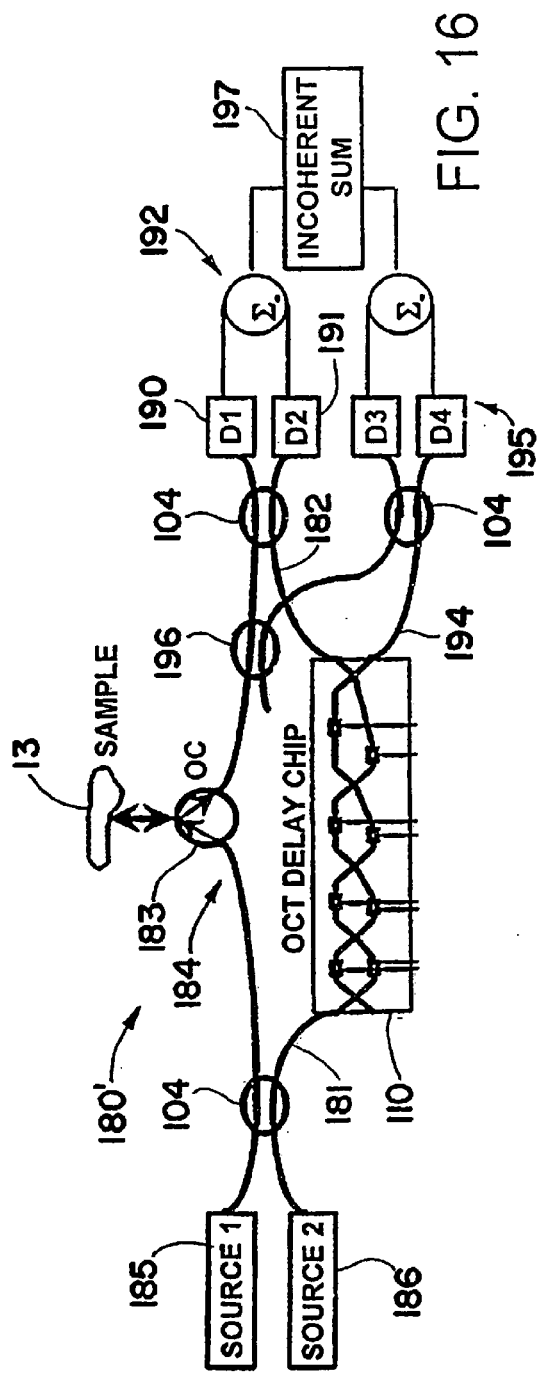
FIG. 15
FIG. 16

3) CAN ALSO USE IN RETROFLECTION ( INCLUDING CIRCULATOR-BASED IMPROVEMENTS )

- DOUBLE DELAYS BUT NOT FREQ. SHIFTS

FREQUENCY-ENCODED PARALLEL OCT AND ASSOCIATED SYSTEMS AND METHODS

BACKGROUND

This invention relates to new methods for performing optical coherence-domain reflectometry (OCDR) and optical coherence tomography (OCT). These new methods will potentially increase the stability and robustness and decrease the manufacturing costs of OCDR and OCT systems. The new inventions feature versions of OCDR and OCT which have no moving parts, can be operated at higher speeds, are much more compact than the current state of the art, and will potentially be much less expensive to manufacture in quantity and to maintain in field operation.

OCDR is a method for determining the positions and amplitudes of optical reflections along an optical axis (called an A-scan) by using low-coherence interferometry. OCDR has been used for characterizing fiber and integrated-optics components and biological tissues. In OCT, the optical beam is scanned laterally across the sample surface while recording A-scans, thus obtaining a two-dimensional map (called a B-scan) of the positions and amplitudes of optical reflections as a function of both depth and lateral positions. OCT has been widely applied for cross-sectional imaging both medical and non-medical applications.

Most previous implementations of OCDR and OCT to date have used some variant of the scanning Michelson interferometer design 10 illustrated in FIG. 1 (at right). In this interferometer 10, light from a low-coherence source 11 is split evenly by a fiber coupler 12 into sample and reference arms 13, 14 of the interferometer. Light returning from the reference arm interferes coherently with light returning from reflections internal to the sample 15 only when the relative path lengths from the beamsplitter 12 to the reflections in each arm are matched to within the source coherence length (the "coherence gate"). For typical biomedical and industrial applications of OCDR and OCT, sources with coherence length on the order of 5–15 micrometers are chosen. In normal operation, the reference arm 14 of the interferometer 10 is scanned at a constant or near-constant velocity. Scanning the reference delay in this manner shifts the frequency of the light returning from the reference arm according to Doppler's equation:

$$f_0 = \frac{V_\phi}{\lambda_0} \qquad (1)$$

Here, f is the shift in the reference light frequency, V is the scan speed of the phase delay in the reference arm ($V_\phi$=2s for a mirror 16 translating with velocity s), and $\lambda_0$ is the center wavelength of the optical source 11. Light returning from the scanning reference delay is mixed with light reflected from various depths in the sample on the surface of a suitable optical receiver 20. The photocurrent generated in this receiver can be characterized as having three separate components: 1) a direct-current (DC) component resulting from light returning from the reference arm 14 (this is usually the largest component and sets the noise level of the resulting measurement); 2) a DC component resulting from light returning from reflections in the sample 15, and 3) an alternating-current (AC) interferometric component resulting from heterodyne mixing of the light returning from the sample and reference arms 13, 14.

The interferometer 10 has a frequency spectrum centered at frequency f, and contains the desired information about the positions and amplitudes of reflections in the sample 15. Typically, signal processing electronics (or alternatively digital signal processing) are provided to separate the information-carrying interferometric component of the receiver 20 signal from the DC components. The separation of the interferometric component from the DC components is accomplished by band-pass filtering or synchronous detection. The signal processing typically includes detection of the envelope of the interferometric signal (either by envelope detection or by synchronous demodulation), followed by further band-pass filtering to reject extraneous optical and electronic noise.

Thus obtained, the envelope of the interferometric signal as a function of the reference arm position represents a map of sample reflectivity versus depth into the sample, and is typically digitized using an A/D converter or dispayed directly on an oscilloscope or an equivalent device. If a two-dimensional image is to be acquired, the beam is scanned across the sample surface between successive A-scans (or equivalently the sample is scanned under the beam), and the data from all of the A-scans acquired are saved as a two-dimensional data set and displayed as a gray-scale or false-color image.

Although the Michelson interferometer topology of OCDR and OCT is still common, several variations of the basic design which allow for illumination of the sample in transillumination, in reflected or scattered directions other than exact backreflection direction, have been reported and demonstrated in recent years. In addition, several variations of the basic OCDR/OCT design which improve imaging efficiency have been disclosed over the past several years. Alternative interferometer designs which make more efficient use of the source light by using unbalanced fiber couplers to direct more than 50% of source light to the sample have recently been described. These designs make use of non-reciprocal optical elements (e.g., optical circulators) to direct the optimal amount of source light to the sample, and to optimally direct light returning from the sample and reference arms to a detector or detector pair.

A high speed scanning optical delay line (ODL) in the reference arm of an OCT system is needed in order to acquire images rapidly. For a review of ODLs which have been applied in OCT, the reader is referred to Rollins, et al. Previously developed ODLs which have been applied to OCT can be classified into four categories. The first category is the class of ODLs that are based on linear translation of retroreflective elements. The second category varies optical pathlength by rotational methods. The third category consists of optical fiber stretchers. The fourth category is based on group delay generation using Fourier-domain optical pulse shaping technology. A severe limitation on the first, second, and fourth categories of ODLs is that they are implemented in bulk optics, necessitating that the reference arm light must be re-coupled into the reference arm singlemode optical fiber after passing through the ODL. This requirement makes the reference arm the most critical optical component to be aligned in the entire OCT system and systems based on these ODLs are very challenging to design, manufacture, and align. This makes such systems very expensive to manufacture and very time-intensive to maintain. OCT systems based on the third category of ODL exhibit a different set of difficulties associated with static and dynamic birefringence effects in stretching fibers. Thus, there is a need for an ODL which is simple, robust, intrinsically fiber-coupled, and inexpensive to manufacture in quantity. The multi-path reference delay network and multipath, frequency-encoded reference delay networks described herein both satisfy this need.

Several OCT system designs have been disclosed which allow for increased robustness in system by performing sample illumination and signal collection within several parallel channels simultaneously. Parallel collection can be effected by collection of light from either a) multiple depths in the sample simultaneously (here termed temporally parallel detection, b) multiple scattered directions from the same depth in the sample (here termed spatially parallel detection, c) multiple laterally separated sites on the sample simultaneously (here termed laterally parallel detection, or some combination of a), b), or c). Designs which have been disclosed previously include temporally parallel detection by using a Fourier-domain approach with array detection called chirp-OCT, spatially parallel detection using CCD arrays, and laterally parallel detection using CCD arrays and photorefractive crystals in combination with array detectors. Unfortunately, the primary drawback of all of the parallel detection techniques disclosed to date is that they all depend upon some form of array detection (using, for example, CCDs or photodiode arrays) to collect the multiple channels of optical signals. The drawbacks of array detection in OCT include: 1) the dynamic range of many array detectors (e.g. CCD arrays) is much less than that of photodiode detectors typically used in OCDR and OCT. Since the DC component in the detected signal in OCDR and OCT typically overwhelms the interferometric component by several orders of magnitude, the dynamic range of the array detector may become filled or nearly filled with the DC component of the signal, leaving little SNR (signal to noise ratio) left for the interferometric component. 2) Even for array detectors with high dynamic range such as photodiode arrays, the signal processing which must be accomplished to remove the DC component of the OCDR/OCT signal and to extract the interferometric component with high SNR must also be accomplished in parallel, which requires the creation of very complicated and expensive parallel signal processing channels. Thus, while parallel detection in OCT is desirable from the point of view enabling imaging with increased system robustness by having no moving parts, there is a need for a parallel implementation of OCT which uses a single rather than an array detector and for which the required signal processing can be carried out using simple algorithms. The frequency-encoded parallel OCT and multi-path, frequency-encoded reference delay networks described herein satisfy this requirement.

A method has also previously been disclosed for obtaining en face OCT images (i.e. images which are oriented parallel to the sample surface rather than as cross-sectional cuts through the sample) at multiple depths simultaneously by splitting the reference arm light and providing for two or more different delays in the split reference path, each of the split paths being modulated at a characteristic carrier frequency (Podoleanu). This could be considered as a form of frequency-encoded parallel OCT. The difference between this approach and the present inventions (FIGS. 1 and 2) is that the prior art allows for only a few discrete frequency-encoded optical delays, each of which is detected using a separate frequency-selected channel, for the purpose of providing multiple, axially distributed, en face images. The present invention approach provides for a large number of frequency-correlated depth channels, for the purpose of rapidly acquiring multiple depth scans of the sample (A-scans) by the much simpler signal processing approach of analyzing the frequency spectrum of the light returning from the detector. The resulting frequency spectrum directly represents the depth-resolved reflectance properties of the sample, without any need for further signal or image processing.

These and other objects, aspects, features and advantages will become more apparent as the following description proceeds.

A number of features are described herein with respect to embodiments of the invention; it will be appreciated that features described with respect to a given embodiment also may be employed in connection with other embodiments.

The invention comprises the features described herein, including the description, the annexed drawings, and the claims, which set forth in detail certain illustrative embodiments. These embodiments are indicative, however, of but a few of the various ways in which the principles of the invention may be employed.

It will be appreciated that the features and principles of the invention may be used in systems other than those disclosed herein for PS-OCT and the like.

Although the invention is shown and described with respect to illustrative embodiments, it is evident that equivalents and modifications will occur to those persons skilled in the art upon the reading and understanding hereof. The present invention includes all such equivalents and modifications and is limited only by the scope of the claims.

DESCRIPTION OF THE DRAWINGS

FIGS. 9A and 9B, respectively, are top and side views of rapid-scan optical delay line (RSOD) with modifications for double passing light;

FIGS. 13B and 13C are, respectively, graphs of the pahse modulator signal and the interferometric signal of the network of FIG. 13A;

FIGS. 15–17 are schematic illustrations of frequency-encoded, multi-path reference delay networks or lines incorporated in OCT systems;

DESCRIPTION

Figure 1:
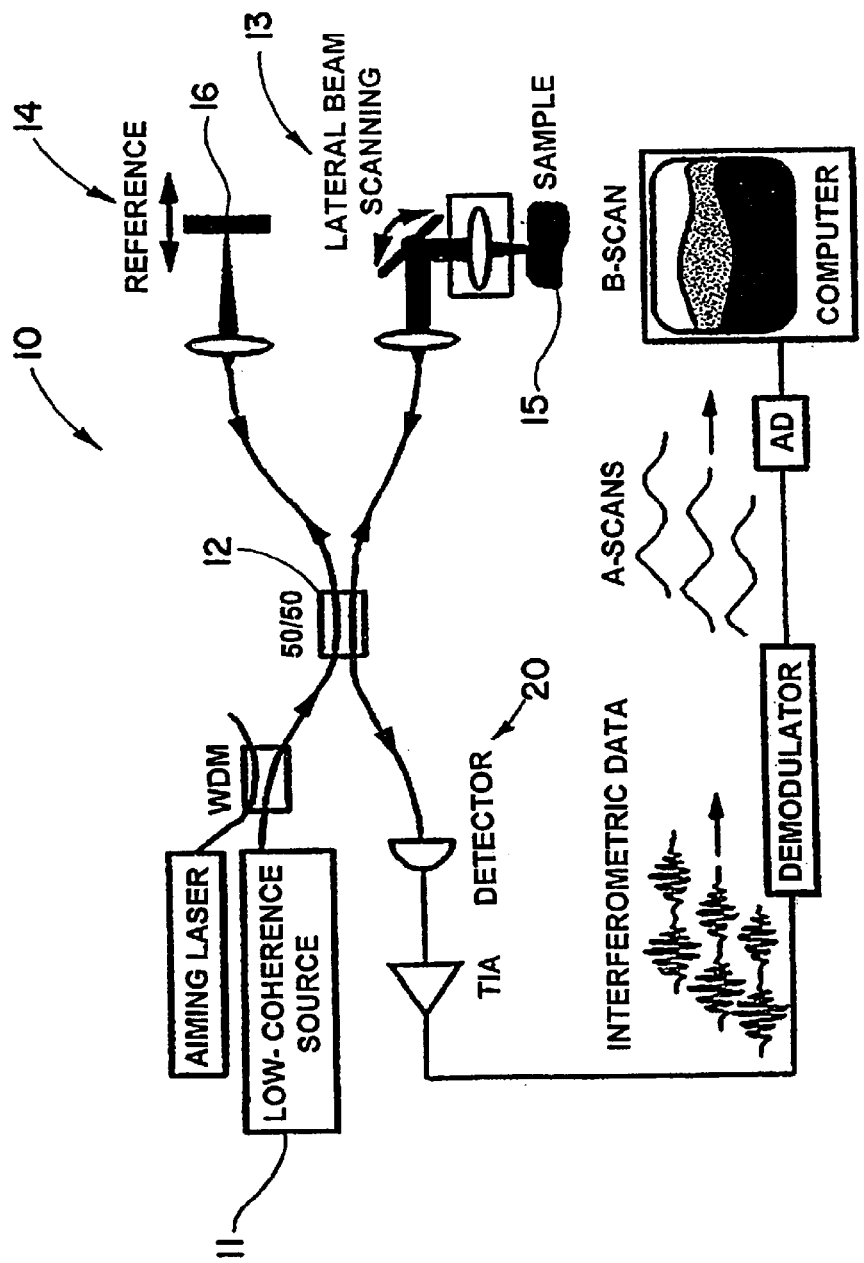
FIG. 1 is a schematic illustration of an OCT system.

In standard OCT, e.g., as is illustrated in FIG. 1, the probe light illuminates all depths, but signal from only one depth at a time is selected by the coherence gate for detection. If signal from several, or all depths could be detected simultaneously, then the pathlength scanning requirements of the delay line could be relaxed, or be unnecessary altogether.

Figure 2:
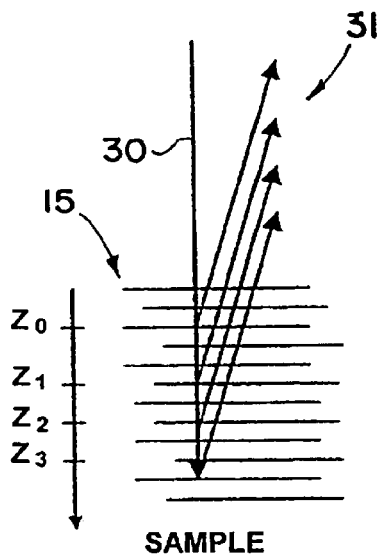
FIG. 2 is a schematic illustration of illumination penetrating or probing a sample at respective depths.

FIG. 2 schematically illustrates the OCT probe beam 30 illuminating the sample 15, and multiple signal beams 31 backscattering from different depths, namely $z_0, z_1, z_2, z_3$, in the sample. In order to detect multiple depths simultaneously, each must be encoded in such a way that they can be differentiated and separated. This encoding could potentially make use of any or several or all of the properties of the probe light wave, namely intensity, phase, frequency, or state of polarization. Intensity is not the optimum property of light on which to encode depth-location information because intensity is already carrying the information about the reflectivity of the sample. State of polarization could encode only two depth locations simultaneously because any state of polarization can be completely described by the linear combination of two orthogonal polarization states. If the depth-location information is encoded in frequency, then signal from multiple depths could be detected in parallel. Signal from different depth locations could then be separated by computing the fast Fourier transform (FFT) of the detected signal, or by any other time-frequency analysis method (e.g. filter banks, matched filtering, chirping, etc.)

One method of achieving frequency-encoding of signal from multiple depths is by use of a multiple-pathlength delay line in the reference arm of the OCT interferometer that imposes a different frequency shift (e.g. Doppler shift) on each different pathlength, or delay. An exemplary reference arm 14 in a conventional interferometer 10 is shown in FIG. 1.

Figure 3:
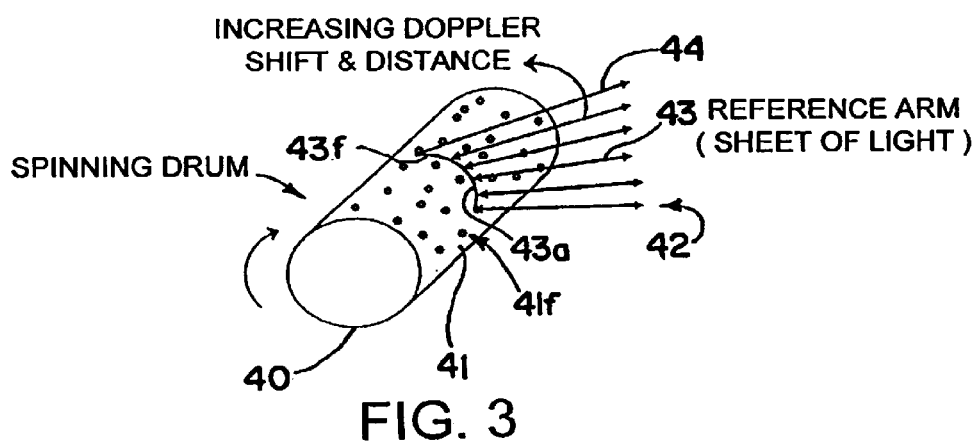
FIG. 3 is a schematic illustration of a scanning delay line source.

One possible multiple-pathlength, frequency encoded delay line is illustrated in FIG. 3. Here, a cylinder 40 is covered with scattering, or ideally, retroreflective material 41. If the cylinder is illuminated by a sheet of light 42 (such as through a slit aperture) then light 43 backscattered from the apex 43a would travel the shortest path, and light 44 backscattered further from the center 44f would travel longer paths. If, in addition, if the cylinder 40 were spinning, then the particles 41f illuminated in different positions would have different velocity components in the direction of the propagation of the light, and therefore would impose a different Doppler shift on light traveling different pathlengths. One possible problem with this design is that it is likely to be inefficient at returning light to the interferometer 10.

Figure 4:
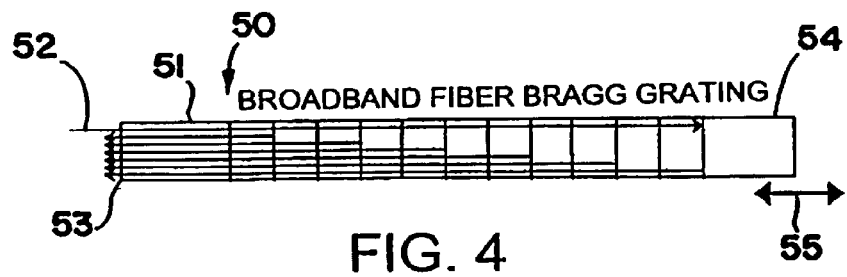
FIG. 4 is a schematic illustration of a stretched fiber delay line source.

Another multiple-pathlength, frequency encoded delay line 50 useful in the reference arm of an interferometer, such as shown in FIG. 1, is illustrated in FIG. 4. Here, a broadband fiber Bragg grating 51 is illuminated by the reference light 52. The nature of Bragg reflection is such that the reflectivity is distributed, in other words portions of the light wave are reflected from different depths, having traveled different pathlengths. If the proximal end 53 of the fiber Bragg grating 51 is held fixed while the distal end 54 is pulled or otherwise is stretched 55, then assuming the elasticity of the fiber is constant, light returning from the proximal reflection sites will have traveled shorter pathlengths and will have been Doppler shifted by smaller frequencies. Light returning from the distal reflection sites will have traveled longer pathlengths and will have been Doppler shifted by higher frequencies.

Figure 5:
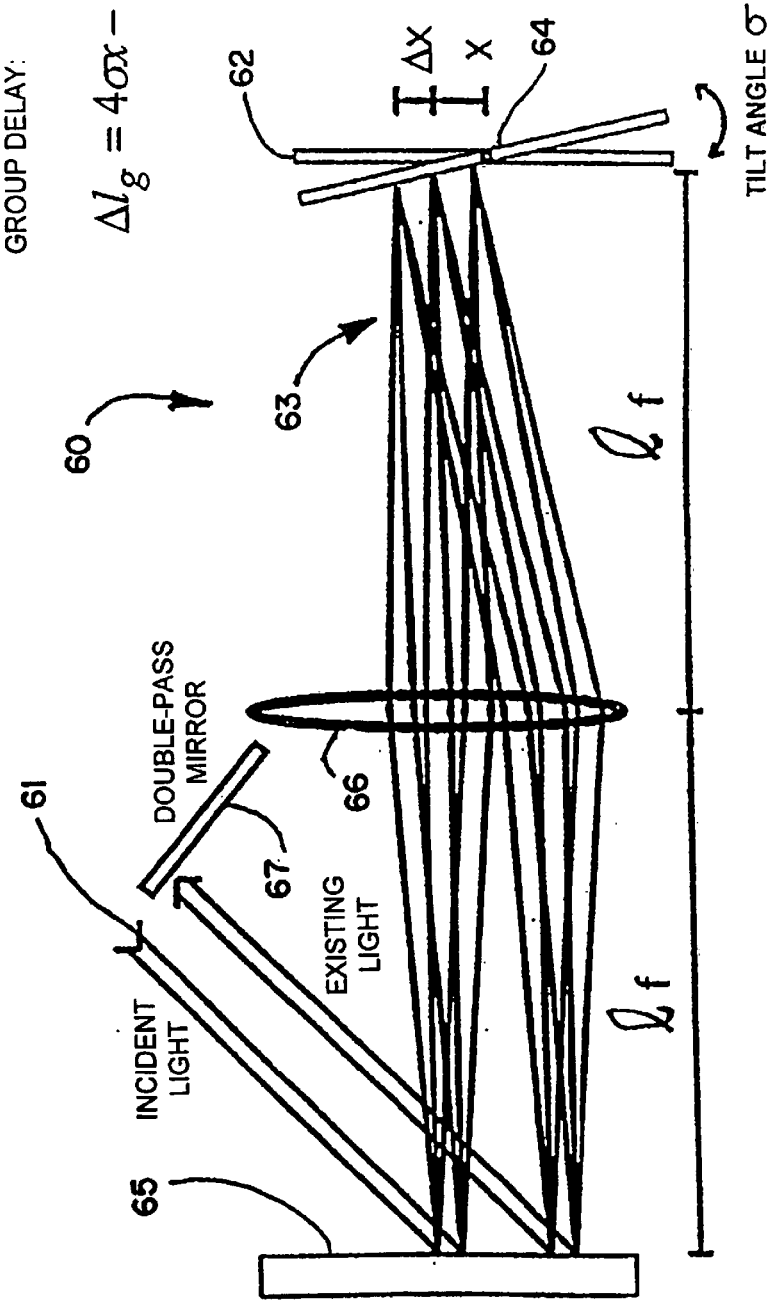
FIG. 5 is a schematic illustration of a rapid-scan optical delay (RSOD)

FIG. 5 illustrates a rapid-scanning optical delay (RSOD) line 60 which operates by imposing a linear phase ramp of varying slope on the spectrum of the light wave 61 by tilting a flat mirror 62 (here shown at two exemplary tilt angles). Because a linear phase ramp on the spectral phase is the Fourier transform of group delay, the tilting mirror 62 effects a group delay on the light wave 61. In addition, if the center wavelength of the spectrum 63 incident on the tilting mirror is offset from the mirror pivot 64, then a net Doppler shift will be imposed on the light wave, resulting in phase delay of the light wave in addition to group delay (Rollins, A. M., et al., *In Vivo Video Rate Optical Coherence Tomography.* Optics Express, 1998. 3(6): p. 219–229). By illuminating the mirror 62 at multiple distances X simultaneously, a range of group delays and a correlated range of carrier frequencies are obtained. Expressions for phase delay and group delay are given in FIG. 5 as a function of mirror tilt angle σ, mirror pivot offset x, lens focal length $l_f$, center wavelength $\lambda_0$, and diffraction grating 65 pitch p. Lens 66 is in the optical path, as shown. This delay line 60 will be the basis of the next several embodiments.

From the drawing of FIG. 5, the mentioned expressions are, as follows: Depends on Fourier transform property:

$$X(t-t_0) \longleftrightarrow X((\omega)e^{-j\omega t_0} \qquad \text{Eq.1}$$

Phase delay:

$$\Delta l_\phi = 4\sigma x \qquad \text{Eq.2}$$

Group delay:

$$\Delta l_g = 4\sigma x - (4\sigma|\lambda_0/p) \qquad \text{Eq.3}$$

Figure 6:
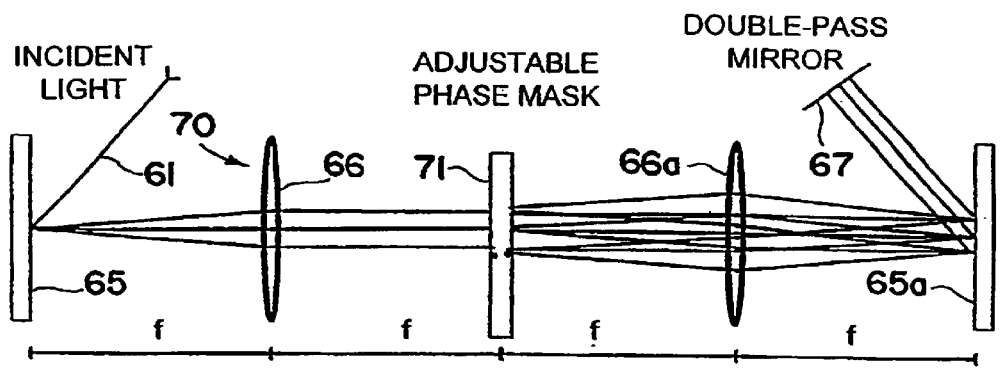
FIG. 6 is a schematic illustration of a multiple pathlength frequency encoded reference arms interferometer.

Another multiple-pathlength, frequency encoded delay line 70 is illustrated in FIG. 6, as an addressable beam-deflector multipath RSOD. Here, the RSOD line 70 illustrated in 5 is unfolded in order to use a transmissive phase mask 71 in the Fourier plane rather than a flat tilting mirror (62 in FIG. 5). As shown, incident light 61 travels through the RSOD line 71 via diffraction grating 65, lens 66, transmissive phase mask 71, lens 66a and diffraction grating 65a to the double-pass mirror 67. If the transmissive phase mask 71 provides a linearly varying phase delay, then a group delay corresponding to the slope of the varying phase delay will be generated. If the slope of varying phase delay is varied in time, then the group delay will be swept in time. If the phase mask 71 provides for the superposition of several phase slopes simultaneously, then each interacts with a portion of the incident light, and then several group delays will be generated simultaneously. For example, this can be achieved by using an acousto-optic (AO) beam deflector as the phase mask 71. If the AO cell is excited with a single frequency, then the traveling acoustic wave acts as a phase ramp (equivalent to beam deflection) and a single group delay is generated. In addition, the light that is delayed also is frequency shifted by the frequency of the acoustic wave. If the AO cell is excited by the superposition of several frequencies, then the resulting superposition of acoustic traveling waves will deflect the light beam in several directions (equivalent to the superposition of several phase ramps), resulting in several simultaneous group delays, each with a different frequency shift. In this way, the device could produce and frequency-encode at least as many independent depth-locations as the AO is capable of producing "resolvable spots". Furthermore, if the AO cell is excited by a signal composed of a continuous spectrum of frequencies, then the light beam will be deflected into a continuum of angles, resulting in a continuum of group delays. Intermodulation effects may impede or even prevent this continuum mode from being implemented successfully.

It is evident from the equations in FIG. 5 that both the phase delay and the group delay of the Fourier-domain rapid-scan optical delay (RSOD) 60 depend upon the distance x by which the center wavelength of the dispersed optical spectrum is offset from the pivot of the scanning mirror. Thus, any method which results in splitting the incident light into several different sub-beams, each of which is separately dispersed into the RSOD and made to be incident at separate values of the pivot offset x on the scanning mirror, will generate a separate group delay and a correlated carrier frequency (the time derivative of the phase delay) for that sub-beam. The method and delay 70 of FIG. 6 is one such approach or method for creating a multiplicity of such sub-beams, one for each desired optical delay in the sample. Two alternative approaches or methods which create a continuous distribution of group delays and associated carrier frequencies are illustrated in FIGS. 7A and 7B.

Figure 7A:
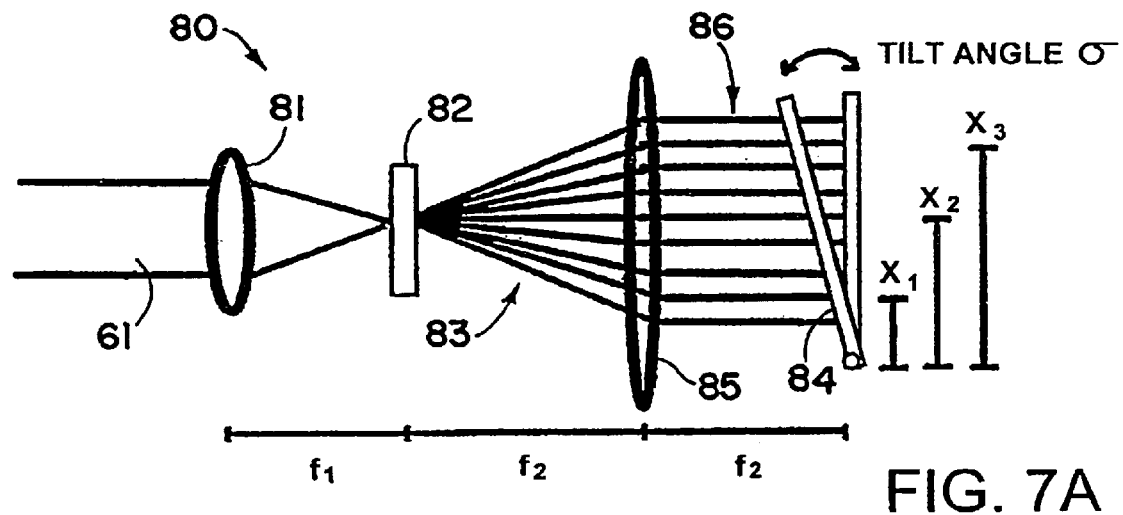
FIGS. 7A and 7B are illustrations on use of lenses in a delay arm.

In FIG. 7A, a positive (convex) cylindrical lens 81 with focal length $f_1$ is placed one focal length in front of the diffraction grating 82 of the RSOD 80. In this case, a transmissive rather than a reflective diffraction grating is used. The lens 81 placed in front of the diffraction grating 82 will create a diversity of sub-beams 83, each one propagating separately through the RSOD and having its center wavelength fall upon a different offset x from the center of the scanning mirror 84. Lens 85 directs light from the diffraction grating 82 to the mirror 84 and from the mirror back to the diffraction grating. The lens 85 may be so positioned and be of the type to provide the illustrated collimating and focusing functions. A cylindrical rather than spherical lens is used for "lens 1 " (81) to preserve the ability to double-pass the multipath RSOD 80, as described in FIG. 9 (below). For example, the center wavelength of three of the sub-beams (from among the continuity of sub-beams 83 generated by lens 81 will fall at positions $x_1$, $x_2$, and $x_3$, as illustrated. Each of these sub-beams will have a different carrier frequency and a slightly different group delay, according to the equations in FIG. 5. In FIG. 7B, a negative (concave) cylindrical lens 81' with focal length $-f_1$ is placed as close as possible to the diffraction grating 82 of the RSOD 80', either in front of or behind it (ideally, the diffraction grating itself would be formed in the shape of a diverging lens). In this case also, a transmissive rather than a reflective diffraction grating is used. The lens 81' placed as near as possible to the diffraction grating 82 will create a diversity of sub-beams 83', each one propagating separately through the RSOD 80' and having its center wavlength fall upon a different offset x from the center of the scanning mirror 84. A cylindrical rather than spherical lens is used for lens 1 (81') to preserve the ability to double-pass the multipath RSOD. For example, the center wavelength of three of the sub-beams (from among the continuity of sub-beams generated by lens 81 will fall at positions $x_1$, $x_2$, and $x_3$, as illustrated. Each of these sub-beams will have a different carrier frequency and a slightly different group delay, according to the equations in FIG. 5.

Figure 7B:
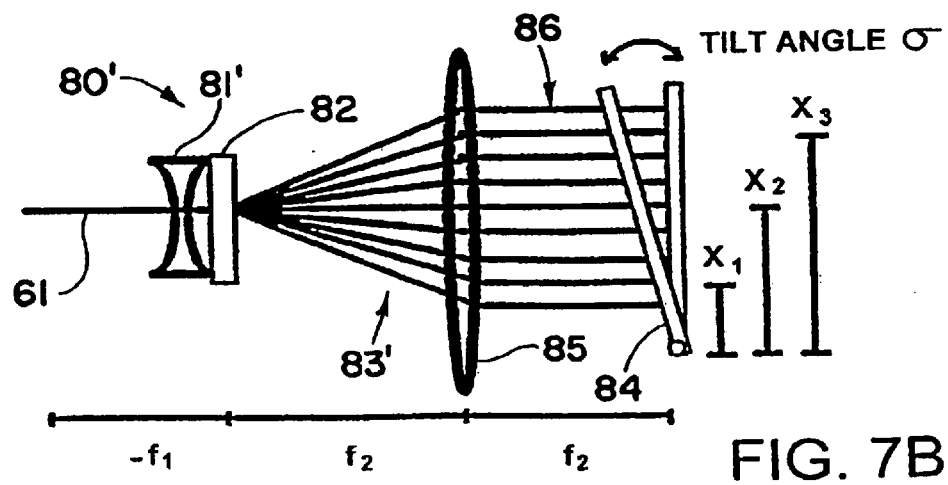
Figure 8A:
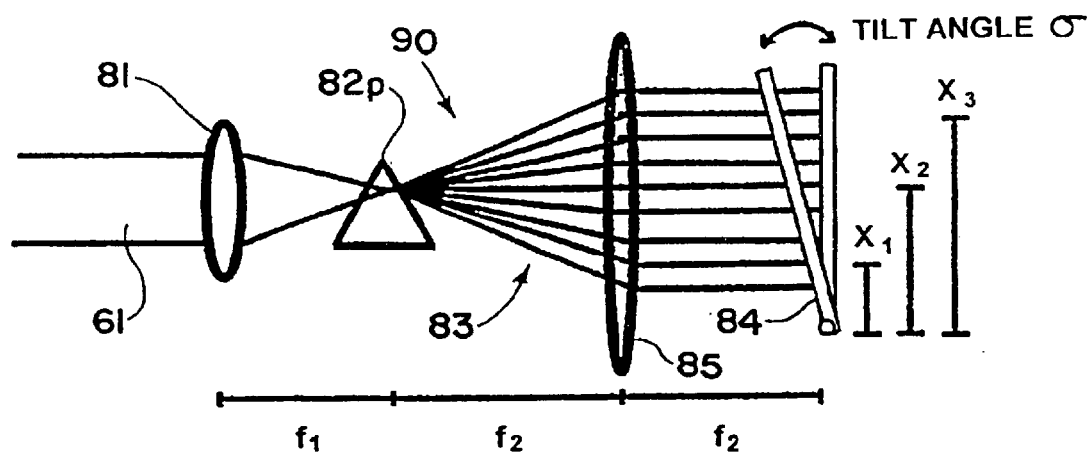
FIGS. 8A and 8B are similar to FIGS. 7A and 7B using prisms.
Figure 8B:
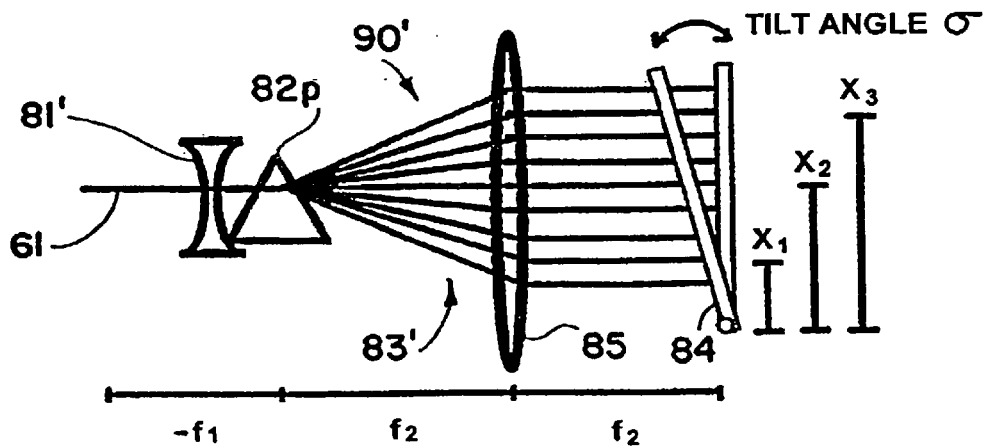

FIGS. 8A and 8B illustrate the same type of approaches and methods of FIGS. 7A and 7B, with the substitution of a prism 82p as the dispersing element of the RSOD 90, 90' in both cases in place of a transmissive diffraction grating, which was used in the RSOD's 80, 80' of FIGS. 7A and 7B. The advantage of using a prism 82p in place of a transmissive diffraction grating is that the prism arrangement would be less lossy of valuable reference arm light since it would disperse all of the light into the proper direction, and not lose any light to higher-order diffraction, which loss may occur using a transmissive diffraction grating. A prism could be used in place of the diffraction grating in conventional rapid-scan optical delay lines, which would result in increased OCDR/OCT system efficiency by being less lossy of reference arm light.

FIGS. 9A and 9B show top and side views of RSOD 80" with modifications for double-passing the frequency-encoded multipath RSOD 80 illustrated in FIG. 7A. Double-passing is well known in RSODs and is desirable because it allows for a greater range of group delays to be obtained. As illustrated in FIG. 9, double passing can be achieved in the multipath RSOD 80" design by tilting the scanning mirror 84 in the vertical dimension, such that the reflected sub-beams 86 pass back through lens 2 (85), the transmissive diffraction grating 82 (or prism 82p as described in FIG. 8, and lens 1 (81), and fall below the incident beam. See the collection of light beams 86'. A separate scanning mirror 84s is placed one focal length away from lens 1 (81), below the incident beam 61, to reflect the recombined sub-beams exactly back along their incident path through the multipath RSOD 80". The second scanning mirror 84s is driven by an appropriate drive waveform which ensures that it is at a scan angle $\sigma_2$ when the first scanning mirror is at scan angle $\sigma_1$, such that all of the sub-beams will be recombined in the diffraction grating 82 or prism 82p (FIGS. 8A and 8B) and will propagate exactly back along the opposite direction as the incident beam 61 and coincident with it.

Multipath, Frequency-encoded Reference Delay Network for OCT (FIGS. 10–17)

Figure 10:
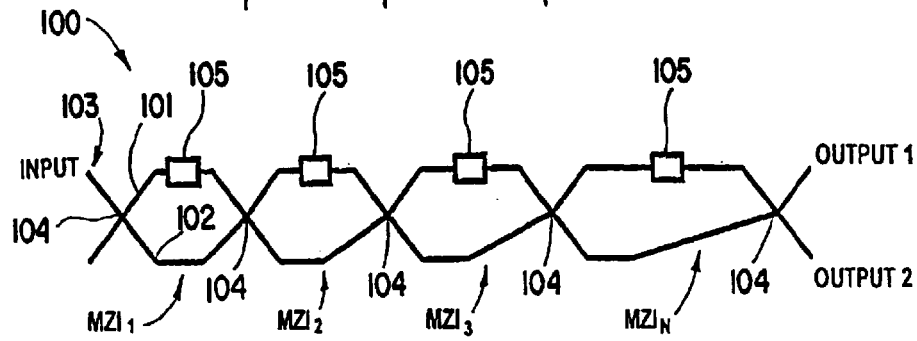
FIG. 10 along with Tables I and II is a schematic illustration of a frequency-encoded reference delay network including cascaded Mach-Zehnder interferometers (MZIs)
Figure 11:
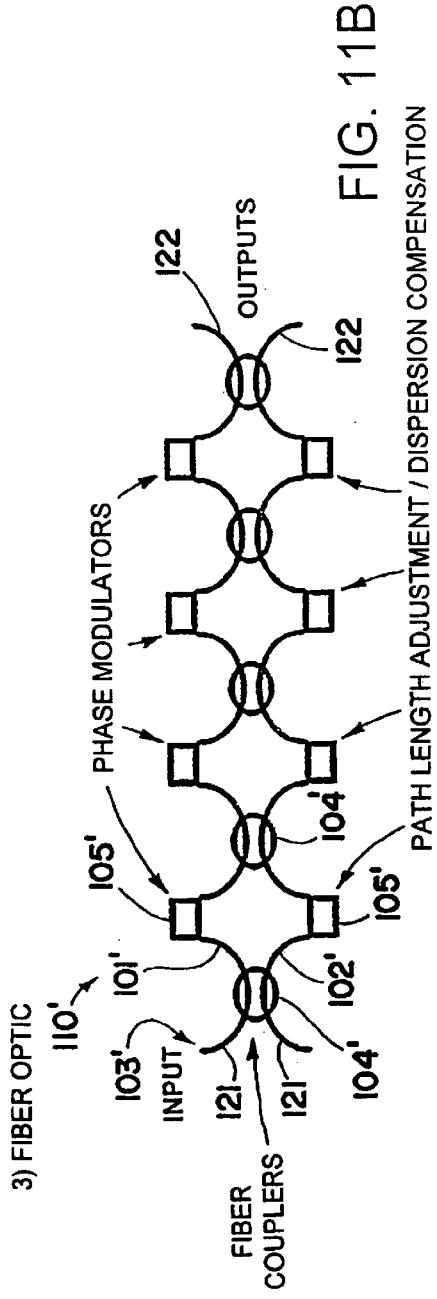
FIGS. 11A and 11B are sechematic illustrations of a multi-path, frequency-encoded delay network in which the MZIs are implemented in bulk optics, fiber optics or integrated optics.

A particularly useful embodiment which makes use of the concept of frequency encoding for depth in OCDR and OCT is illustrated in FIG. 10.

A multi-path, frequency-encoded reference delay network can be implemented in bulk optics, fiber optics, or integrated optics as described below. Several advantages of the multi-path, frequency-encoded reference delay network are as follows. First, in any of its implementations, the delay network achieves detection of optical reflections from a range of depths in a sample simultaneously by encoding reflected signals from each depth with a unique carrier frequency. This frequency-encoded parallel depth detection allows for depth imaging without any moving parts, thus improving the robustness and reliability of OCT systems. Second, the signal processing required to extract the depth-resolved reflectivity of samples from the frequency-encoded signal is relatively simple, and can be implemented with standard techniques and instruments for spectral analysis of signals such as spectrum analyzers and Fourier transforms. Third, the integrated-optic implementation of the multi-path, frequency-encoded reference delay network could be very small, robust, and inexpensive to produce and maintain in quantity.

A multi-path, frequency-encoded reference delay network 100 includes a cascade of N Mach-Zehnder interferometers (MZIs) as illustrated in FIG. 10 and the associated tables thereof. Each of the MZIs is specified to have unequal path lengths between its two arms 101, 102, such that the path length difference is greater than the coherence length of the OCDR/OCT light source (not shown) that provides input light to the input 103 of the network 100. With each MZI unbalanced in path length by at least $l_c$, the power exiting each MZI via respective beam splitters 104, e.g., 50/50 splitters (or some other splitter, if desired) in the cascade will be equally split between the inputs of each subsequent MZI. The path length difference in the Ith MZI is given by $2^{I-1}$ times the fundamental unit of delay of the delay network, here referred to as $l_c$ (standing for the coherence length of the optical source). It is to be understood that the coherence length represents the minimum value which could be chosen for the fundamental unit of delay, and larger values could be selected which would correspond to a coarser sampling of depth in the resulting OCDR or OCT system. The longer arm of each of the MZIs in the frequency-encoded reference delay network also contains a frequency shifter 105, which imposes a frequency shift on the light propagating through that arm proportional to the path length difference in that MZI. The basic unit of frequency shift corresponding to the fundamental unit of delay is here denoted as $f_0$. As described below, a preferred method for implementing the frequency shifter is to incorporate an electro-optic phase modulator into the long arm of each MZI, driven by a specific voltage waveform (described in FIG. 12 and explained below). If this is done, then the shorter arm of each MZI would preferably include an identical phase modulator, to assure dispersion matching in both arms of the MZI and to provide for independent balancing of each MZI against phase imbalances caused by manufacturing defects, temperature variations, etc.

By the method described here, each possible path through the cascade of MZIs accumulates a unique differential path length (as compared to the path which goes through the short arm of all of the MZIs), as well as a unique total frequency shift which is proportional to that differential path length. A delay network with N basic MZI elements will thus have MZI path length differences and associated frequency shifts equal to $2^{I-1} \cdot l_c$ and $2^{I-1} \cdot f_0$, respectively, for the stages given by I=1, . . . N. The MZIs may be cascaded in ascending, descending, or any alternate order of pathlength difference and frequency shift.

In the example of reference delay network 100 illustrated in FIG. 10, there are N=4 MZIs, thus the differential path lengths and frequency shifts of each stage are given by $l_c$, $f_0$(I=1), $2l_c$, $2f_0$(I=2); $4l_c$, $4f_0$(I=3), and $8l_c$, $8f_0$(I=4=N). Thus, all of the possible $2^N$ paths through the entire network tabulated in FIG. 10 will be illuminated, and the light propagating through each individual path will be encoded with its own total frequency shift (given by the sum of the frequency shifts in each of the MZI arms through which it propagates) which is proportional to its total differential path length (relative to some default length of the short arm of each MZI, $l_0$). Thus, $2^N$ path lengths ranging from $N \cdot l_0$ to $N \cdot l_0 + 2^{N-1} \cdot l_c$ and $2^N$ frequency shifts ranging from 0 to $2^{N-1} \cdot f_0$ will all be illuminated simultaneously in the network 100. For N stages, there will be $2^N$ paths through the network 100 (with the light split evenly between them all), and the frequency shifts sum to form $2^N$ corresponding frequencies. Thus, the depth-resolved reflectivity of the sample (i.e., the A-scan) of the sample object 13 (FIG. 1), for example, will be directly represented in the frequency spectrum of the detected output, with no reference scanning required at all.

It should be understood that the assignment of frequency shifts to the long arm of each MZI, by incorporation of the frequency shifter there, is just one example of how path lengths may be coded into frequencies in the current invention. If frequency shifters were incorporated into both arms of each MZI, another equally valid approach would be to impose a positive frequency shift proportional to the differential path length in the long arm of each MZI, and a negative frequency shift proportional to the differential path length in the short arm. It is not even necessary to have each integral multiple of $l_c$ be encoded into the same integral multiple of $f_0$, although signal processing of the resulting waveforms would certainly be simplified if that were the case. The important point is to associate some specific frequency shift with each path length difference, whatever that assignment is.

FIGS. 11A and 11B illustrate a multi-path, frequency-encoded reference delay network 110 in which the MZI's are implemented in bulk optics, fiber optics, or integrated optics. In a bulk optic implementation, the 50/50 splitters 104 (assumed to be placed at every intersection of optical paths in the Figure) could be 50/50 cube or thin-film beamsplitters, the optical paths 101, 102 (the solid lines in the Figure), for example, would propagate through free space, and the phase modulators 105 could be phase modulators manufactured from Lithium Niobate or other electro-optic materials. The drawbacks of a bulk-optics implementation would be that the delay network 110 would be relatively difficult to align and also would be relatively lossy, since many discrete optical elements would be used. In FIG. 11B a fiber optic implementation 110', the 50/50 splitters 104' could be singlemode fused fiber couplers, the optical paths 101', 102' could be singlemode optical fibers, and the phase modulators 105' could be integrated-optic, piezo-electric, or electrostrictive phase modulators. Some of the phase modulators, e.g., those at the bottom of FIG. 11B, could be used for path length adjustment/dispersion compensation. The fiber-optic embodiment 110' would have the advantage of being very power efficient (fused fiber couplers are readily available with <0.6 dB insertion loss) and relatively low cost, however this embodiment would be relatively difficult to manufacture due to the difficulties in fusing multiple fiber couplers together with sufficiently accurately controlled path lengths. In FIG. 11A an integrated-optic implementation 110, the entire delay network 110d including N MZIs could be implemented into a single substrate such as Lithium Niobate, a hybrid polymer/glass-based chip technology, or any other suitable integrated-optic substrate 120. As illustrated in FIG. 11A, such an integrated-optic OCT "delay chip" 110 would have an input singlemode fiber 121 permanently bonded ("pigtailed") to it, would have N or 2N inputs (depending on whether one or two phase modulators 105 are provided per MZI—two being shown as the example only), and would have one or two output fiber pigtails 122 corresponding to the outputs of the last MZI in the network. Some of the phase modulators, e.g., those shown at the bottom of FIG. 11A, may be used as phase shifters for delay offset or dispersion compensation. The advantages of the integrated-optic embodiment are that it could be very small, could be fiber pigtailed in the factory using established techniques (obviating the need for field alignment of any aspect of an OCT system), and could be mass produced at relatively low unit cost.

Figure 12:
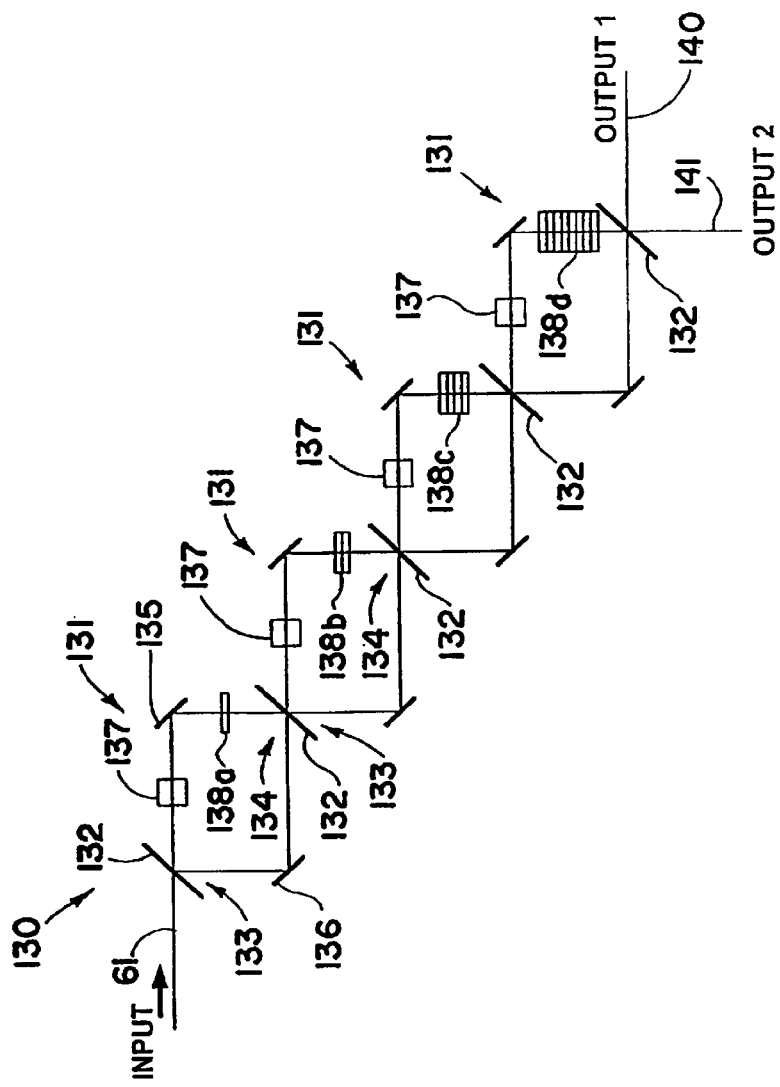
FIG. 12 is a schematic illustration of a bulk optic implementation of a 4-stage multi-path, frequency-encoded delay network.

An illustration of a bulk-optic implementation of a 4-stage multipath, frequency-encoded reference delay network 130 is illustrated in FIG. 12. In this figure, four bulk-optic MZIs 131 are illustrated in a rectangular configuration, each having a beamsplitters (BS) 132 at its input 133 and output 134 and each also have two mirrors (M) 135, 136 to redirect the beams in the interferometer arms toward the next MZI. Each MZI contains at lease one phase modulator (PM) 137 acting as a frequency shifter. Optionally, an additional phase modulator may be placed in the other arm of each MZI for phase balancing purposes. Each successive MZI has a delay element 138a–138d of optical pathlength $l_c$, $2 l_c$, $4 l_c$, and 8 $l_c$, placed in its frequency shifted arm. These delay elements consist of some material with a different group delay index than air, such as glass. Light outputs 140, 141 are provided via the beam splitter 132 of the MZI in the last stage of the network 130.

Figure 13A:
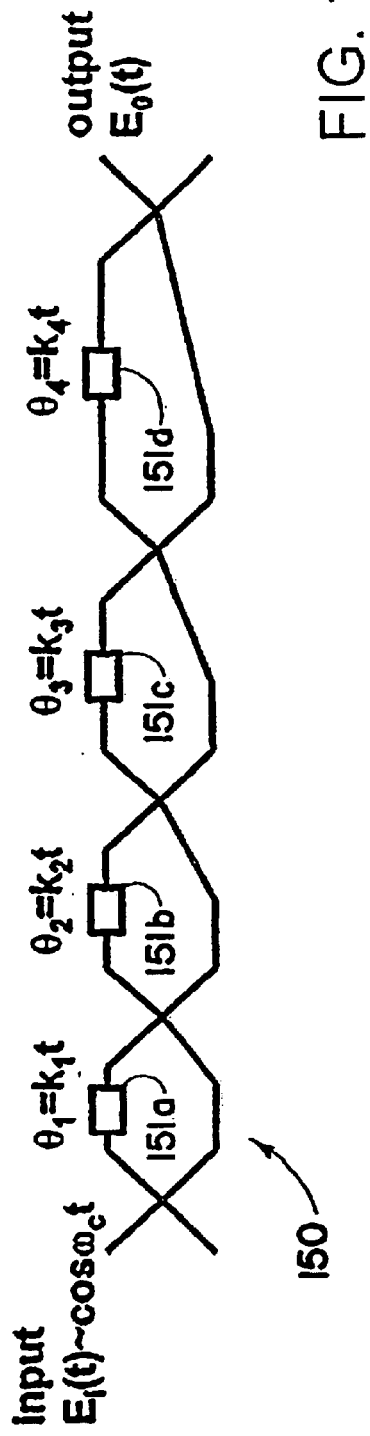
FIG. 13A is a schematic illustration of an electro-optic phase modulator asa single-sideband frequency shifter in a multi-path, frequency-encoded reference delay network.

The frequency shifters included in the multi-path, frequency-encoded reference delay networks produce a sufficiently clean, single-sideband modulation of the reference arm light such that when multiple frequency shifts are cascaded together, there will be minimal cross-talk between adjacent multiples of frequency $f_0$. As examples only, two current frequency-shifting technologies that meet this requirement are illustrated in FIG. 13A. First, acousto-optic frequency shifters could be used. However, acousto-optic frequency shifters have the drawbacks that they produce relatively high modulation frequencies (that could be downshifted by a second accousto-optic modulator (AOM)), and there is some difficulty in integrating them into integrated-optic devices. A more preferred approach would be to synthesize frequency shifting by supplying an appropriate drive waveform to a phase modulating device, such as an electro-optic phase modulator (for fiber-optic or integrated-optic embodiments) or a piezo-electric fiber stretcher (for fiber-optic embodiments).

The use of an electro-optic phase modulator as a single-sideband frequency shifter in multi-path, frequency-encoded reference delay network 150 is illustrated in FIG. 13A. We assume that the electric field incident on the delay network has the form $E_i(t)=\cos \omega_c t$, where $\omega_c$ is the light wave center angular frequency and t is time. Phase modulators 151a–d the four illustrated placed in stages I=1, ... 4 of the multi-path, frequency-encoded reference delay network 150 are driven by linear drive voltage waveforms such that their phase delays at any instant are given by $\theta_I = k_I \cdot t$, where k is a constant proportional to the slope of the drive waveform applied to each phase modulator. Then, the electric field of the light wave having traversed each of the phase modulators will be given by:

$$E_0(t) = \cos(\omega_c t + \theta_1 + \theta_2 + \theta_3 + \theta_4);$$

$$\cos[(\omega_c + k_1 + k_2 + k_3 + k_4)t].$$

Thus, all of the phase modulators acting together generate a total frequency shift given by $k_n = k_1 + k_2 + k_3 + k_4$, which will modulate the desired OCDR/OCT interferometric signal at this same frequency. Since $E_0(t)$ is a cosinusoidal function, the same frequency shift will be generated by a $2\pi$-periodic waveform (meaning a waveform which generates a phase delay linearly varying between 0 and $2\pi$ phase delay, repetitively), as illustrated in FIG. 13A, as would be generated by a continuously increasing phase, since it is only the slope of the phase increase which determines the frequency shift. Thus, pure single-sideband frequency shifting may be accomplished using sawtooth phase modulation represented by curve 155 (FIG. 13B), so long as the sawtooth drive function has sufficiently high duty cycle. The interferometric signal is illustrated by curve 156 (FIG. 13C).

Figure 14A:
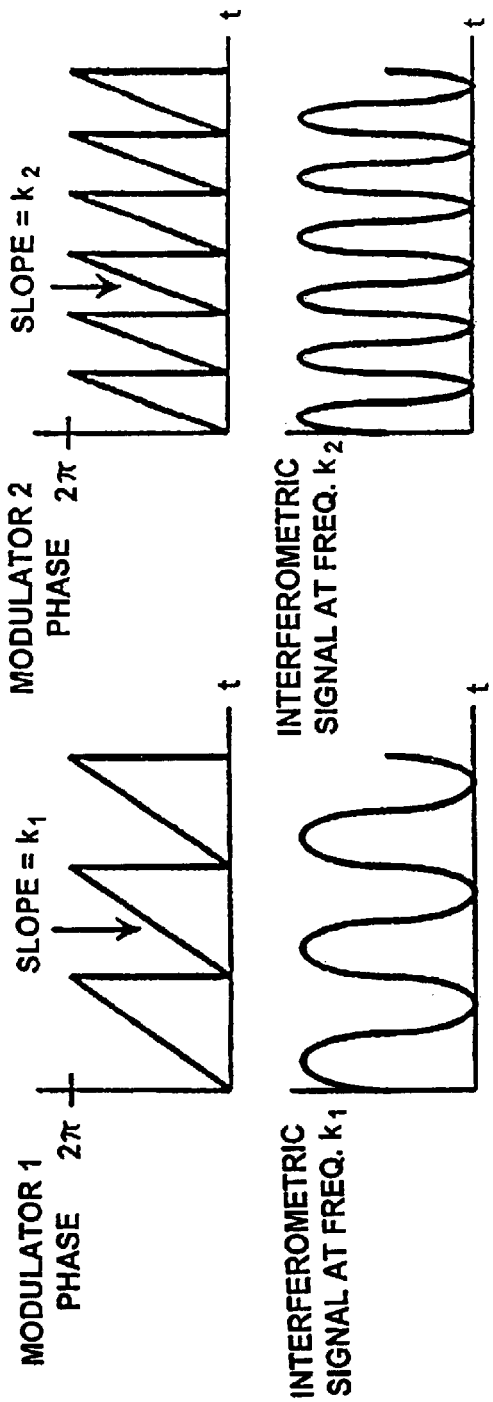
FIGS. 14A and 14B are graphs of signals describing or representing operation of the network of FIG. 13A.
Figure 14B:
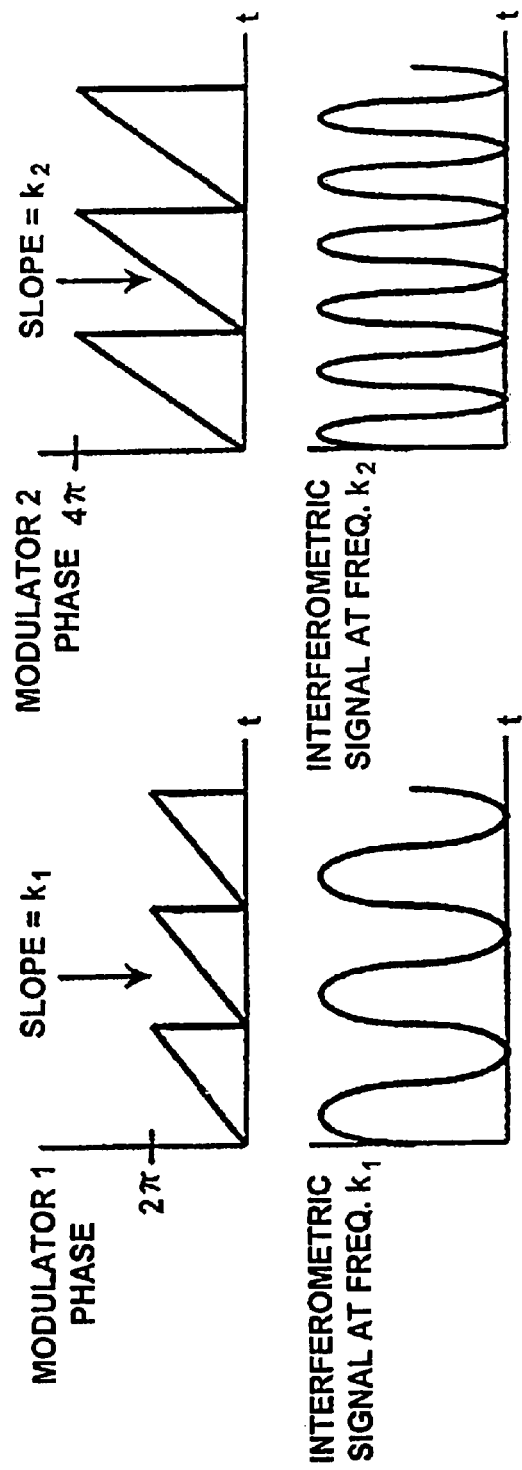

FIGS. 14A and 14B describes two methods for simultaneously generating the integral multiples of the frequency shift $f_0$ which are required in the multi-path, frequency-encoded reference delay network described above. To generate multiple frequency shifts simultaneously using phase sawtooth approach, in the first approach (FIG. 14A), each phase modulator is driven with a $2\pi$ periodic waveform as just described, each having its own drive waveform slope $k_I$.

The principal drawback to this approach is that N separate radio-frequency drivers/amplifiers would be required. A preferred approach, illustrated in FIG. 14B, would be to use a single radio-frequency driver operating at some convenient drive waveform slope, say $k_1$, and then to multiply or divide down the amplitude of this waveform by integral amounts to drive the other phase modulators. To generate multiple frequency shifts simultaneously using phase sawtooth approach, in the example illustrated in FIG. 14B, the waveform generating a modulation of amplitude $2\pi$ on modulator 1 is doubled in amplitude to generate a modulation amplitude of $4\pi$ on modulator 2, thus generating twice the frequency shift. An advantage to this latter approach is only need one RF driver at maximum amplitude (other amplitudes are derived from voltage divider network).

The "delay chip" 110d disclosed in FIG. 11A is a frequency-encoded, multi-path transmissive delay with dual outputs 122, each of which will have equal optical power. Since most typical OCT systems are built using reflective optical delay lines, we here disclose three methods by which the frequency-encoded, multi-path transmissive delay could be incorporated into OCT systems. In FIG. 15, the frequency-encoded, multi-path transmissive delay 110 (or 110', 130, 150, etc.) is incorporated into an OCT system 180 based on a Mach-Zehnder rather than a Michelson interferometer topology. In this topology, the input 181 and one of the outputs 182 of the OCT delay chip 110 is used as a transmissive delay, and an optical circulator (OC) 183 is used in the sample arm 184 to enable detection of exact backscattering (reflections back into the incident direction) from the sample 13. One or two optical sources 185, 186 may be used, and two detectors 190, 191 may be used in a dual-balanced differential configuration 192 to eliminate common-mode noise and provide an output at a meter or other output device 193.

The embodiment network 180' of FIG. 16 is very similar to FIG. 15 but makes better use of the available source power by directing the other output 194 of the OCT delay chip 110 into a second differential detection channel 195. Both outputs of the delay chip are caused to interfere with light reflected from the sample 13 by splitting that light using an additional fiber coupler 196. The signals resulting from each differential detection channel 192, 195 are then incoherently summed at 197.

Figure 17:
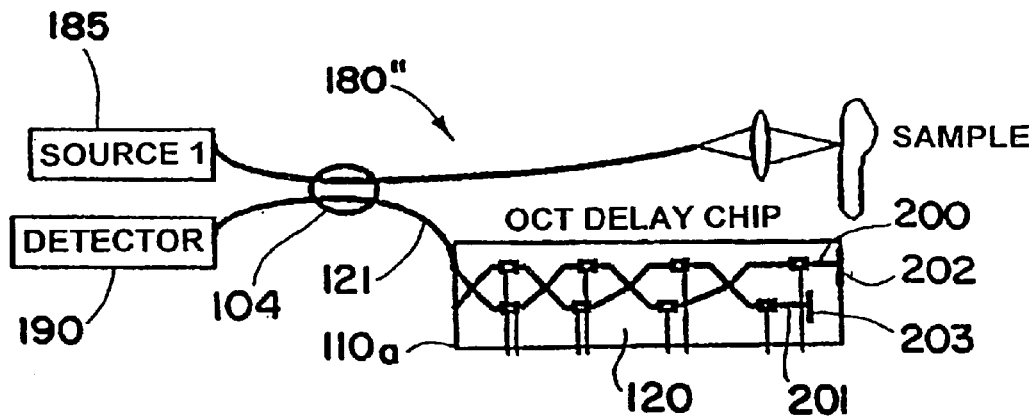

The embodiment network 180" illustrated in FIG. 17 uses the OCT delay chip 110a as a reflective optical delay line by reflecting the light at the multi-path reference delay network outputs 200, 201 back through the network 180". This may be accomplished by placing mirrors 202, 203 external to the OCT delay chip 110a, or preferably by coating such mirrors directly onto the edge of the integrated-optic substrate 120. If the mirrors are coated with an identical phase delay on each output of the last MZI, then all light will be reflected reciprocally back through the entire multi-path reference delay network 180", and will emerge from the input fiber 121 with a pathlength delay equal to twice the delay of the network operating as a transmissive delay. The network 180" with the reflective OCT delay chip 110a doubles the delays but not the frequency shifts.

It should be understood that FIGS. 15 and 16 are just two illustrations of the use of the multi-path reference delay network as a transmissive delay in OCDR and OCT, and many other interferometer designs may be possible which require a transmissive delay.

It should be understood that FIG. 17 is just one illustration of the use of the multi-path reference delay network as a reflective delay, and it may equally well be used in other inteferometer designs which use reflective delays including those which use nonreciprocal optical elements for sensitivity improvement.

It should be understood that bulk-optic and fiber-optic embodiments of the multi-path, frequency-encoded reference delay network types may also be used in the interferometer configurations described in FIGS. 15–17 and in alternative related inteferometer topologies described above.

Multipath Reference Delay Network for OCT (FIGS. 18–24)

In FIGS. 1–21 is illustrated an approach or method for achieving reference delay scanning in OCT, wherein the multi-path reference delay network is a temporally scanned optical delay line much like the scanning optical delays which are currently widely used in OCT such as scanning retroreflectors or a Fourier-domain rapid-scan optical delay (RSOD), rather than frequency-encoded parallel version of OCT, which was described above. The multi-path reference delay network can be implemented in bulk optics, fiber optics, or integrated optics as described below. Three advantages of the multi-path reference delay network are as follows: First, in any of its implementations, the delay network can be switched very rapidly, generating very fast delay scanning. Second, since it performs scanning of reference delay as a function of time, the multi-path reference delay network could be retrofitted into existing OCT systems without any change in the requirements or algorithms for signal processing. Third, the integrated-optic implementation of the multi-path reference delay network could be very small, robust, and inexpensive to produce and maintain in quantity.

Figure 18:
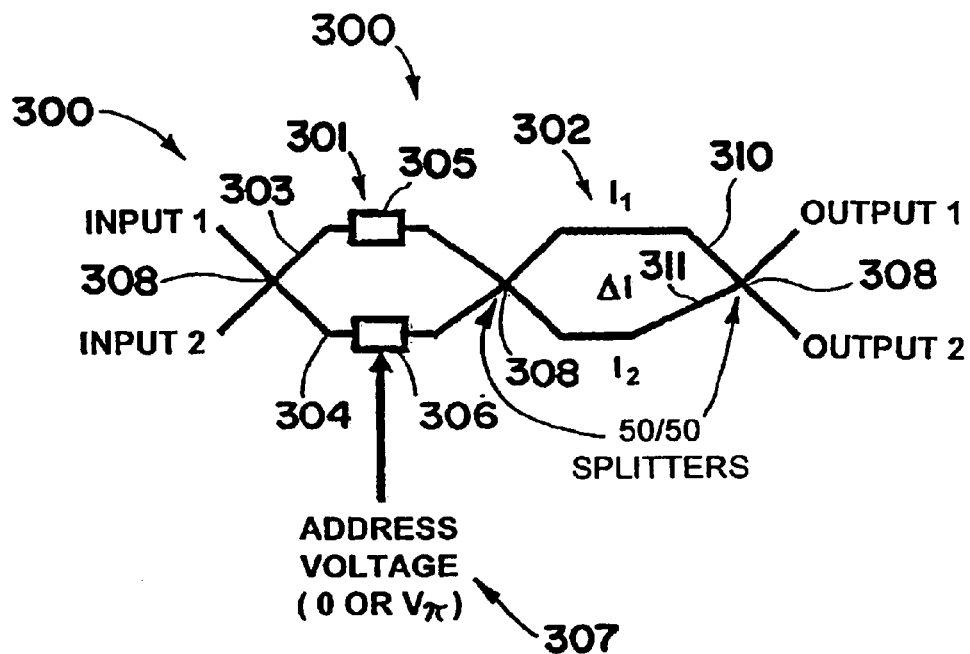
FIGS. 18–21 are schematic illustrations of temporally scanned optical delay lines for use in delay scanning in OCT.

The basic element or unit 300 of the multi-path reference delay network 300' is illustrated in FIG. 18. The basic element is a pair of Mach-Zehnder interferometers 301, 302 (a "control interferometer" and a "delay interferometer"), in which the first interferometer acts as an addressable switch to direct light into one of two possible branches of the second interferometer with the desired delay. The control interferometer 301 has equal optical path lengths in both arms 303, 304, such that the amount of optical power directed into either arm of the delay interferometer 302 is a function of the difference in optical phase accumulated by light traversing both paths of the control interferometer. This phase, and the resulting path selected in the delay interferometer 302, is selected by one (or preferably two) phase modulators 305, 306 placed in one (or preferably both) arms of the control interferometer 301. The phase delay in either modulator is set by application to that modulator of a control voltage 307, being either zero (for no modification of the path selected), $V_\pi$, the voltage required to change the phase by $\pi$ radians or 180 degrees or some other voltage determined by the relative phases of the waves incident on the two inputs of the control interferometer 301. Provision of a second phase modulator in the other path of the control interferometer 301 is not absolutely necessary for selection of the path in the delay interferometer, but is preferable to be supplied to assure dispersion matching in both arms of the control interferometer and to provide for independent balancing of each control inteferometer against phase imbalances caused by manufacturing defects, temperature variations, etc. Provision of a second balancing modulator would also ease the requirements on the modulator power supply and switching circuitry, since the differential phase delay required for addressing of the control inteferometer could also be achieved by application of a suitable differential voltage to both phase modulators. Beam splitters 308 are at the junctions of respective arms, as shown; exemplary splitters are 50/50 splitters.

The second ("delay") Mach-Zehnder interferometer 302 in the basic unit 300 of the multi-path reference delay network 300' has unequal path lengths, such that the path length difference between the arms 310, 311 of the delay interferometer 302 is greater than the coherence length of the OCDR/OCT light source 11 (for example—see FIG. 1), and is given by to $2^{I-1}$ times the fundamental unit of delay of the addressable delay line, where I is the stage of the basic element 300 in the delay network 300'. The fundamental unit of delay is here referred to as $l_c$ (standing for the coherence length of the optical source), although it is to be understood that the coherence length represents the minumum value which could be chosen for the fundamental unit of delay, and larger values could be selected which would correspond to a coarser sampling of depth in the resulting OCDR or OCT system. The multi-path reference delay network 320 (FIG. 19) is constructed from N cascaded basic elements 300, each comprising control and delay interferometers 301, 302, and with each delay interferometer having a different optical delay. Light inputs 321, 322 and outputs 323, 324 are provided. A delay network with N basic elements 300 will have path length differences in the second interferometer equal to $2^{I-1} \cdot l_c$, for I=1, . . . N, either in ascending, descending, or any alternate order.

Figure 19:
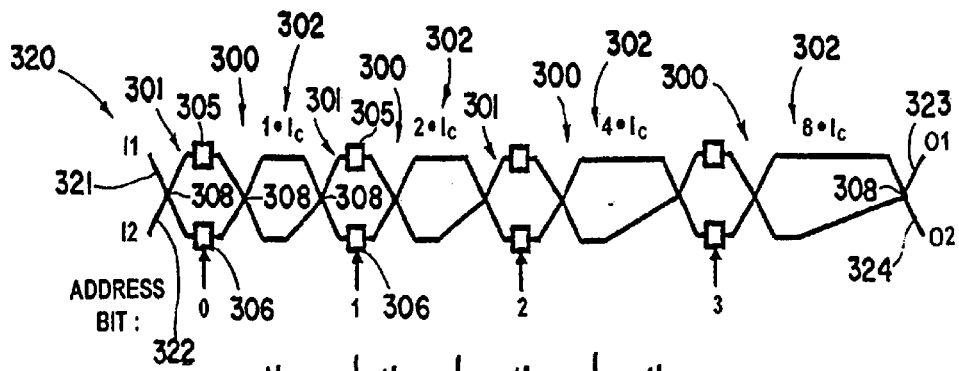

In the example illustrated in FIG. 19, there are N=4 basic elements 300, and the path lengths of each stage are given by $l_c$ (I=1), $2l_c$ (I=2), $4l_c$ (I=3), and $8l_c$ (I=4=N). By appropriate addressing of the phase delay in each control interferometer 301, any of the possible $2^N$ paths through the entire network tabulated in FIG. 19 may be selected. In this way, the differential voltage applied to each control inteferometer in the network may be thought as a single address bit which selects the long path in the associated delay inteferometer (given, for example, by $2^{I-1} \cdot l_c$) when set, and which selects the short path (given by some default length of the short arm $l_0$) when cleared. In this way, $2^N$ paths ranging from $N \cdot l_0$ to $N \cdot l_0 + 2^{N-1} \cdot l_c$ may be arbitrarily selected by setting and clearing of the associated control bits.

The control and delay interferometers 301, 302 of the multi-path reference delay network could be implemented in bulk optics, fiber optics, or integrated optics, as illustrated in FIGS. 20–24. In a bulk optic implementation, the 50/50 splitters (assumed to be placed at every intersection of optical paths in the Figure, e.g., FIG. 19) could be 50/50 cube or thin-film beamsplitters, the optical paths (the solid lines in the Figure) would propagate through free space, and the phase modulators 305, 306 could be phase modulators manufactured from Lithium Niobate or other electro-optic materials. The drawbacks of a bulk-optics implementation would be that the delay network would be relatively difficult to align and also would be relatively lossy, since many discrete optical elements would be used.

Figure 21:
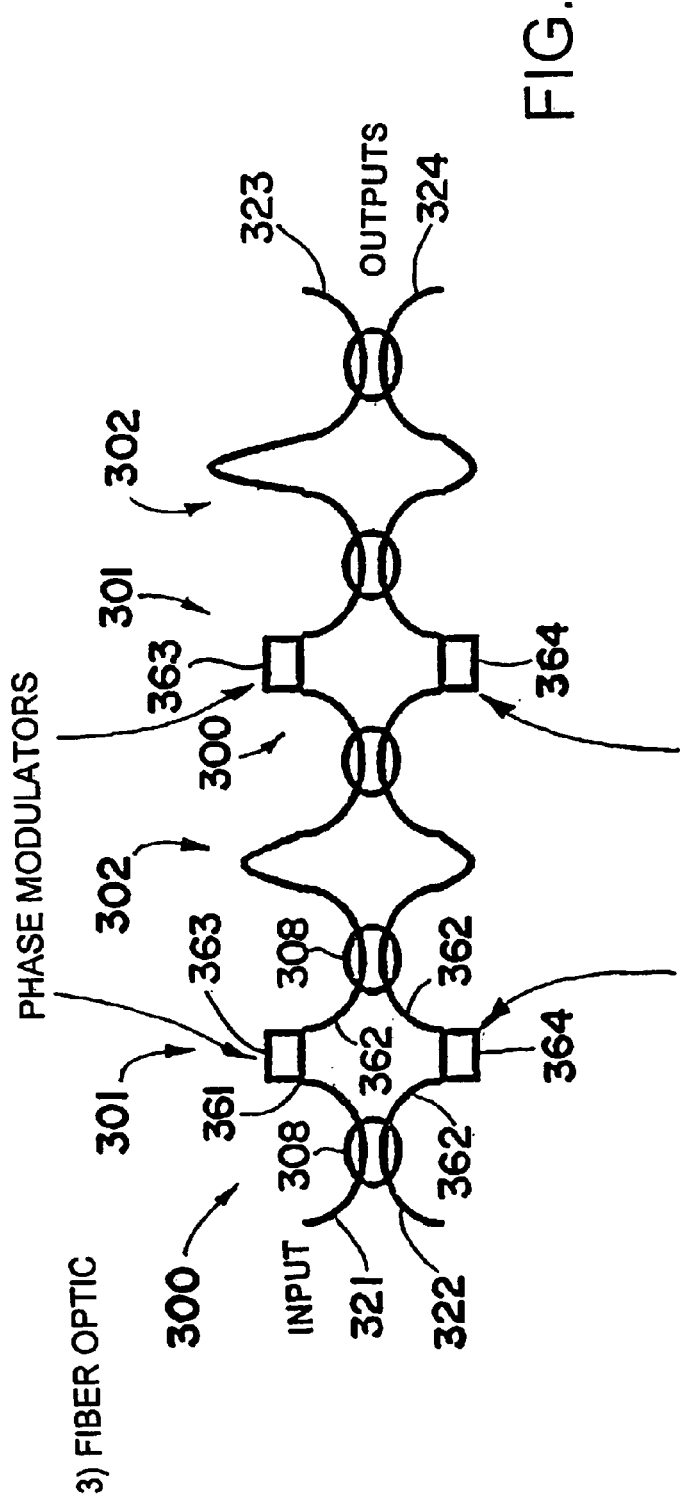

In a fiber optic implementation 360 of FIG. 21, the 50/50 splitters 308 could be singlemode fused fiber couplers, the optical paths 361, 362 could be singlemode optical fibers, and the phase modulators 363, 364 could be integrated-optic, piezo-electric, or electrostrictive phase modulators. The fiber-optic embodiment 360 of delay network would have the advantage of being very power efficient (fused fiber couplers are readily available with <0.6 dB insertion loss) and relatively low cost, however this embodiment would be relatively difficult to manufacture due to the difficulties in fusing multiple fiber couplers together with sufficiently accurately controlled path lengths.

Figure 20:
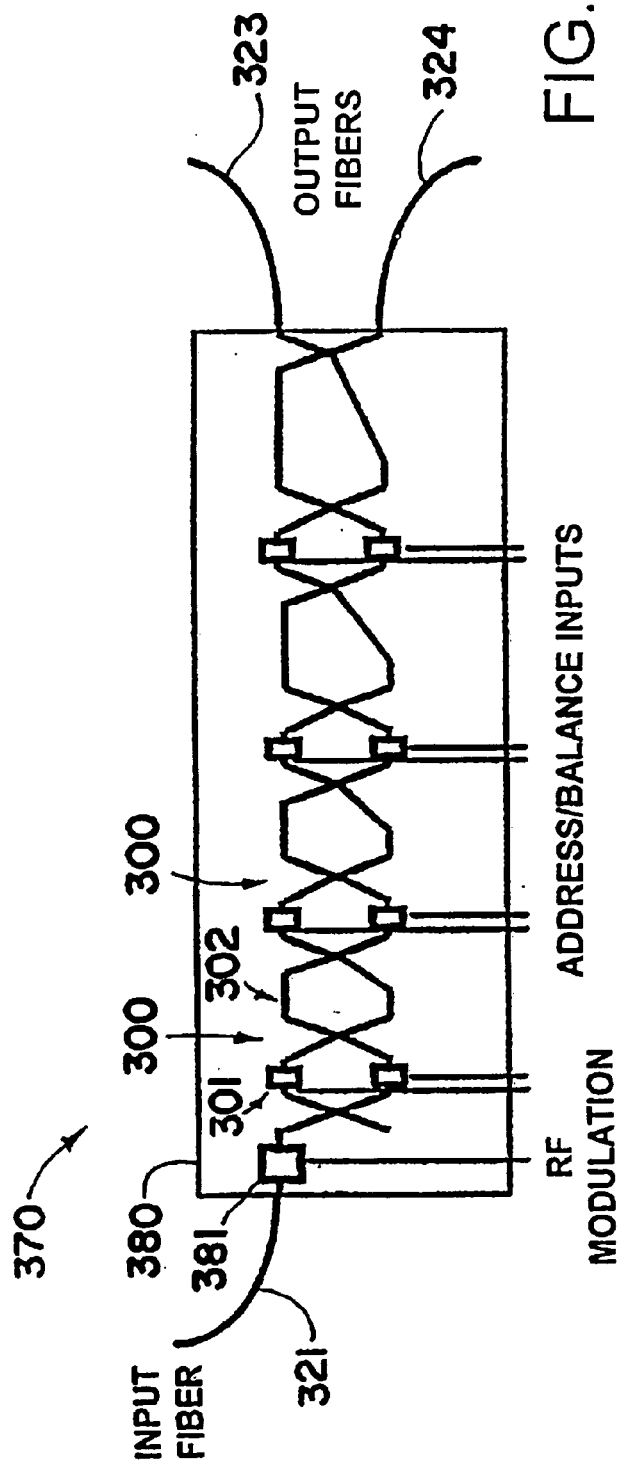

In an integrated-optic implementation 370 of delay network (FIG. 20), which would be the preferred embodiment, the entire delay network 370 consisting of N basic elements 300 could be implemented into a single substrate such as Lithium Niobate, a hybrid polymer/glass-based chip technology, or any other suitable integrated-optic substrate. As illustrated in FIG. 20, such an integrated-optic OCT "delay chip" 380 would have an input singlemode fiber 321 permanently bonded ("pigtailed") to it, could have an additional phase modulator 381 on the input for overall reference arm carrier generation, would have N or 2N inputs (depending on whether one or two phase modulators 363, 364 are provided per control inteferometer 301), and would have one or two output fiber pigtails 323, 324 corresponding to the outputs of the last delay interferometer 302 in the network. The advantages of the integrated-optic embodiment are that it could be very small, could be fiber pigtailed in the factory using established techniques (obviating the need for field alignment of any aspect of an OCT system), and could be mass produced at relatively low unit cost.

Figure 22:
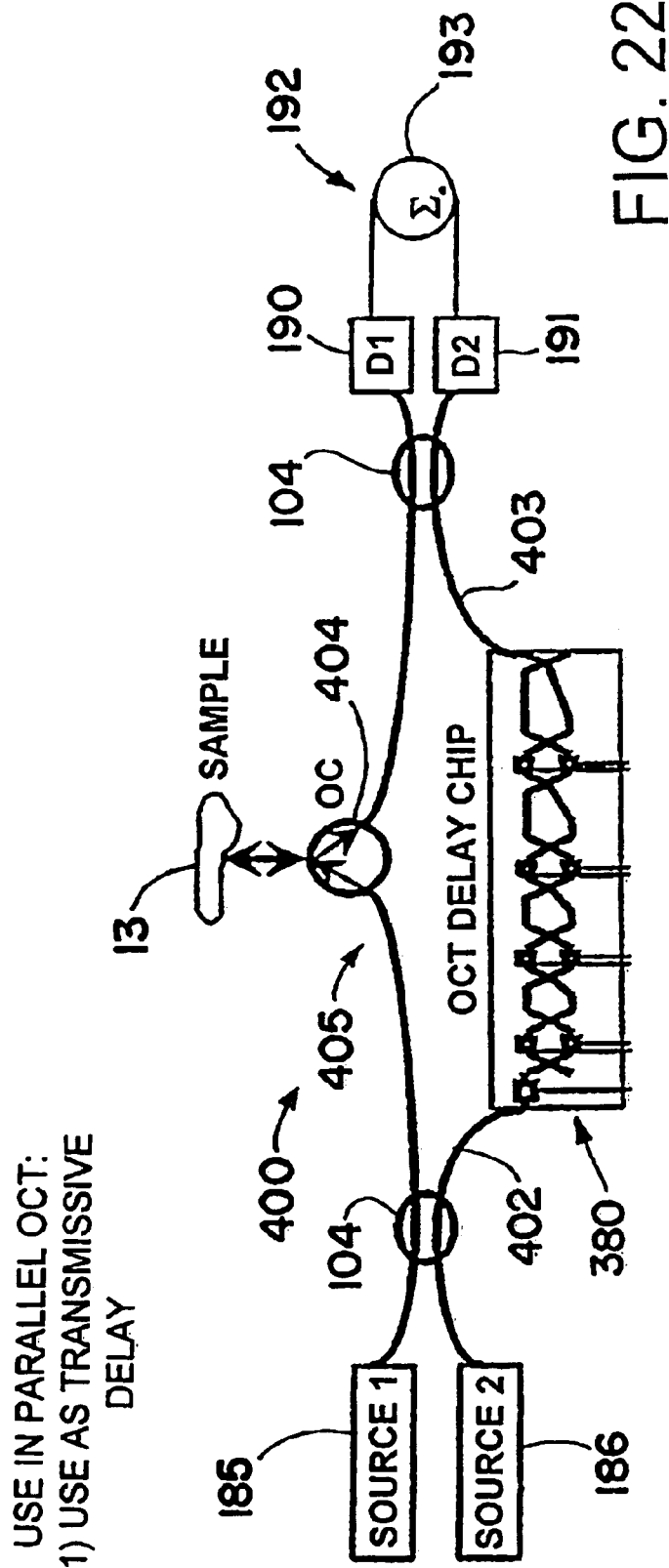
FIGS. 22–24 are schematic illustrations of OCT systems using an OCT delay chip.

The "delay chip" 380 disclosed in FIG. 20 is an addressable transmissive delay with dual outputs, each of which will have equal optical power. Since most typical OCT systems are built using reflective optical delay lines, we here disclose three methods by which the addressable transmissive delay could be incorporated into OCT systems. In the system of FIG. 22, the transmissive optical delay 401 is incorporated into an OCT system 400 based on a Mach-Zehnder rather than a Michelson interferometer topology. In this topology, the input 402 and one of the outputs 403 of the OCT delay chip is used as a transmissive delay, and an optical circulator (OC) 404 is used in the sample arm to enable detection of exact backscattering (reflections back into the incident direction) from the sample. One or two optical sources 185, 186 may be used, and two detectors 190, 191 may be used in a dual-balanced differential 192 configuration to eliminate common-mode noise.

Figure 23:
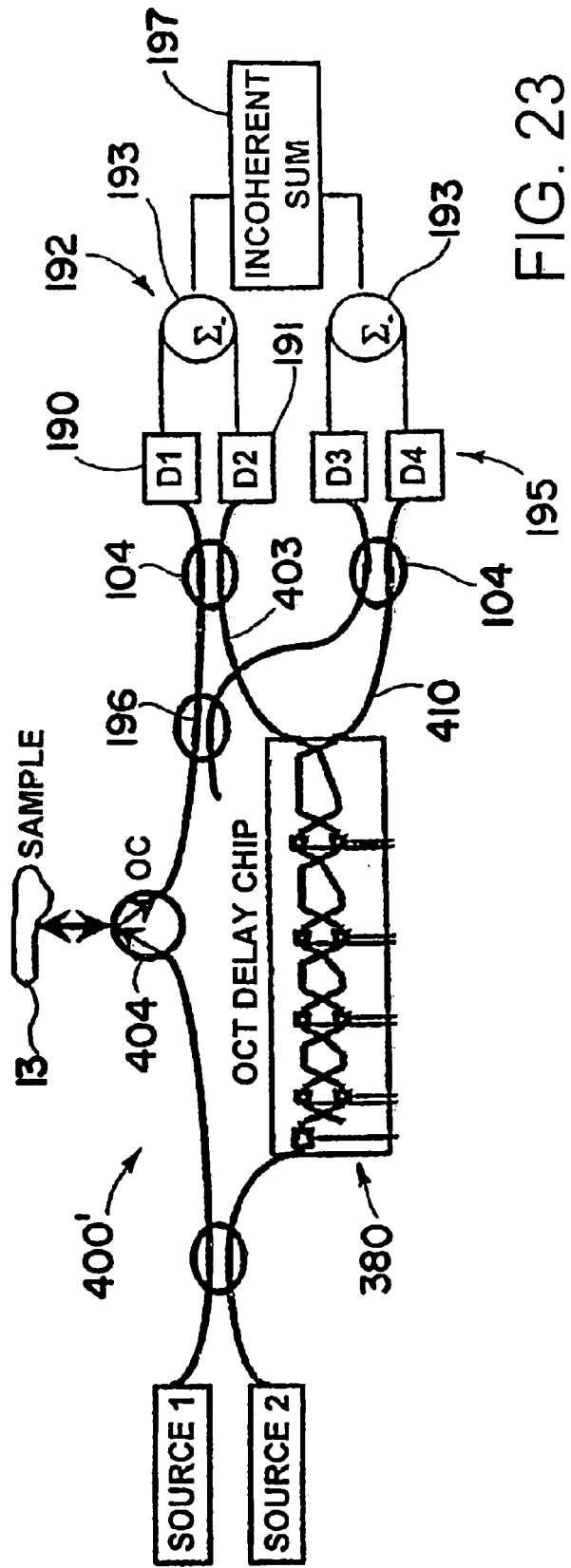

The embodiment 400' of FIG. 23 is very similar to FIG. 22 but makes better use of the available source power by directing the other output 410 of the OCT delay chip output into a second differential detection channel. Both outputs of the delay chip are caused to interfere with light reflected from the sample by splitting that light using an additional fiber coupler 196. The signals resulting from each differential detection channel are then incoherently summed.

Figure 24:
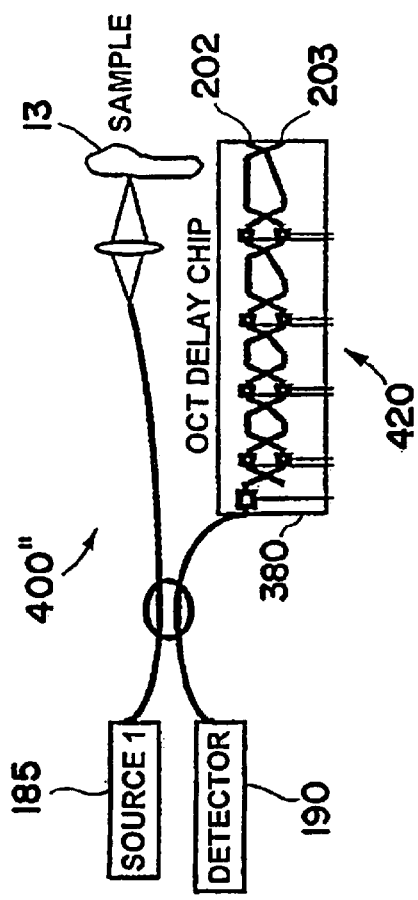

The final embodiment 400" illustrated in FIG. 24 uses the OCT delay chip 380 as a reflective optical delay line 420 by reflecting the light at the multi-path reference delay network outputs back through the network. This may be accomplished by placing mirrors 202, 203 external to the OCT delay chip 380, or preferably by coating such mirrors directly onto the edge of the integrated-optic substrate. If the mirrors are coated with an identical phase delay on each output of the last delay interferometer, then all light will be reflected reciprocally back through the entire multi-path reference delay network, and will emerge from the input fiber with a pathlength delay equal to twice the delay of the network operating as a transmissive delay.

It should be understood that FIGS. 22 and 23 are just two illustrations of the use of the multi-path reference delay network as a transmissive delay in OCDR and OCT, and many other interferometer designs may be possible which require a transmissive delay.

It should be understood that FIG. 24 is just one illustration of the use of the multi-path reference delay network as a reflective delay, and it may equally well be used in other inteferometer designs which use reflective delays including those which use nonreciprocal optical elements for sensitivity improvement.

It should be understood that bulk-optic and fiber-optic embodiments of the multi-path reference delay network types may also be used in the interferometer configurations described in FIGS. 22–24 and in alternative related inteferometer topologies described above.

We claim:

1. An OCT system, comprising an illumination source, reference and sample arms, and a detector, and characterized in that the reference arm substantially simultaneously creates a plurality of reference delays for scanning a sample at respective depths, and wherein the depth information is encoded into frequency.

2. The system of claim 1, further characterized in comprising a computing instrument coupled to respond to signals detected by the detector to provide a Fourier transform analysis of the optical spectrum of the detected signal.

3. The system of claim 1, said computing instrument being operable to map spectrum into distance information relative to depth in a scanned sample.

4. The system of claim 1, characterized in that the reference arm has a plurality of different respective lengths with respective frequency characteristics.

5. The system of claim 4, further characterized in that the reference arm lengths and respective frequency characteristics associated therewith are coordinated to provide information concerning depth in frequency space.

6. The system of claim 1, further characterized in that the delay is distributed over a distance representative of the range of depths to be scanned in a sample.

7. The system of claim 1, further characterized in that the plurality of reference delays are obtained from respective locations on a round reflector.

8. The system of claim 1, further characterized in that the plurality of reference delays are obtained from a Bragg grating.

9. The system of claim 1, further characterized in that the plurality of reference delays are obtained from a stretched fiber that creates a Doppler shift as a function of length along the stretched fiber.

10. The system of claim 9, further characterized in that the fiber is a single mode fiber.

11. The system of claim 1, further characterized in that the delays are encoded in the geometry of the optics of the system.

12. The system of claim 1, further characterized in that the difference in delays are representative of a carrier frequency, and the carrier frequency is of a magnitude in the hundreds of kilohertz through megahertz.

13. The system of claim 1, further characterized in that the reference arm includes a rapid-scan optical delay having a diffraction grating for separating incident illumination to respective wavelength components, a focusing lens, and a scanning reflector, wherein the focusing lens directs light to the scanning reflector, the scanning reflector directs light back through the focusing lens to the diffraction grating.

14. The system of claim 13, further characterized in comprising a double pass reflector for reflecting light back to the diffraction grating, focusing lens, and scanning reflector ultimately to be directed in a path leading to the detector.

15. The system of claim 13, characterized in that the scanning reflector is pivoted in the center.

16. The system of claim 13, characterized in that the reflector is pivoted at an end.

17. The system of claim 1, further characterized in that the reference arm includes a rapid-scan optical delay having a diffraction grating for separating incident illumination to respective wavelength components, a lens, and a scanning device to delay respective wavelengths by different respective amounts.

18. The system of claim 17, further characterized in that the scanning device is an accoustooptic device.

19. The system of claim 17, further characterized in that the scanning device is an electrooptic scanning device.

20. The system of claim 17, further characterized in that the lens is a collimating lens, and further characterized in comprising a further lens for receiving light from the scanning device and directing the light to a further diffraction grating.

21. A method of scanning a sample using an OCT system including an illumination source, reference and sample arms, and a detector, characterized in substantially simultaneously creating a plurality of reference delays for scanning a sample at respective depths, and wherein the depth information is encoded into frequency.

22. The method of claim 21, characterized in comprising in response to signals detected by the detector computing a Fourier transform analysis of the optical spectrum of the detected signal.

23. The method of claim 21, said computing comprising mapping spectrum into distance information relative to depth in a scanned sample.

24. The method of claim 21, characterized in that the reference arm has a plurality of different respective lengths with respective frequency characteristics, and coordinating the reference arm lengths and respective frequency characteristics associated therewith to provide information concerning depth in frequency space.

25. The method of claim 21, characterized in that the different respective lengths are obtained by light reflected from different distances on a curved surface.

26. The method of claim 21, characterized in that the different respective lengths are obtained using a Bragg grating.

27. The method of claim 21, characterized in that the different respective lengths are obtained by stretching a fiber and reflecting light from different locations along the stretched fiber.

* * * * *